United States Patent
Gaynor et al.

(10) Patent No.: US 9,717,811 B2
(45) Date of Patent: *Aug. 1, 2017

(54) FLEXIBLE MULTI-PANEL STERILIZATION ASSEMBLY WITH SIDE TABS

(71) Applicant: AVENT, INC., Alpharetta, GA (US)

(72) Inventors: Melissa R. Gaynor, Roswell, GA (US); Eric T. Bricker, Roswell, GA (US); Jeffrey J. Farmer, Roswell, GA (US); Mark T. Pamperin, Cumming, GA (US); Corinna Schwarz, Roswell, GA (US); Catherine J. Turnbow, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 145 days.

This patent is subject to a terminal disclaimer.

(21) Appl. No.: 13/629,488

(22) Filed: Sep. 27, 2012

(65) Prior Publication Data

US 2013/0081355 A1  Apr. 4, 2013

Related U.S. Application Data

(60) Provisional application No. 61/541,655, filed on Sep. 30, 2011, provisional application No. 61/677,546, (Continued)

(51) Int. Cl.
*B65D 65/26* (2006.01)
*B65D 27/00* (2006.01)
(Continued)

(52) U.S. Cl.
CPC .............. *A61L 2/26* (2013.01); *A61B 50/00* (2016.02); *A61B 50/33* (2016.02)

(58) Field of Classification Search
CPC .............................................. A61L 2202/181
(Continued)

(56) References Cited

U.S. PATENT DOCUMENTS 789,957 A * 5/1905 Bassinger .................... 229/92.7
1,198,676 A * 9/1916 Snyder ......................... 229/92.5
(Continued)

FOREIGN PATENT DOCUMENTS

GB           2274823 A     8/1994
JP         2002362625 A    12/2002
WO      WO 2012/104811 A1   8/2012

OTHER PUBLICATIONS

Co-pending U.S. Appl. No. 13/629,521, filed Sep. 27. 2012, by Gaynor et al. for "Flexible Multi-Panel Sterilization Assembly With Mass Balancing Side Tabs."

*Primary Examiner* — Derek Battisti
(74) *Attorney, Agent, or Firm* — Dority & Manning, P.A.

(57) ABSTRACT

A multi-panel sterilization assembly that includes a barrier panel formed of permeable material having barrier properties, side tabs that include grip portions for folding or unfolding the barrier panel; and a fold protection panel. The barrier panel has a first end and a second end opposite the first end, a first edge and a third edge, each such edge being generally perpendicular to the first end, and a midpoint to generally delineate the barrier panel into a content receiving region extending from approximately the first end to the midpoint and a content covering region extending from the midpoint to approximately the second end. The side tabs are located between the first end and the midpoint of the barrier panel and at or near the first edge and the third edge. The fold protection panel is in juxtaposed communication with the barrier panel such that after folding the content covering region and the first and third edges over the content receiving region, the fold protection panel covers them.

13 Claims, 19 Drawing Sheets

Related U.S. Application Data filed on Jul. 31, 2012, provisional application No. 61/678,751, filed on Aug. 2, 2012.

(51) Int. Cl.
*B65D 75/00* (2006.01)
*A61L 2/26* (2006.01)
*A61B 50/00* (2016.01)
*A61B 50/33* (2016.01)

(58) Field of Classification Search
USPC .................. 229/87.05, 92.5, 87.01, 92.7
See application file for complete search history.

(56) References Cited

U.S. PATENT DOCUMENTS

| | | | |
|---|---|---|---|
| 1,278,115 A * | 9/1918 | Darr .................. | B65D 27/22 229/84 |
| 1,565,178 A | 12/1925 | Mackovjak | |
| 1,720,721 A * | 7/1929 | Culotta .................. | 229/314 |
| 2,224,607 A | 12/1940 | Petzold | |
| 3,073,436 A | 1/1963 | Burt | |
| 3,225,920 A | 12/1965 | Reilly | |
| 3,409,121 A * | 11/1968 | Taterka .................. | 206/299 |
| 3,419,136 A | 12/1968 | Pratt | |
| 3,680,772 A | 8/1972 | Hoover | |
| 3,746,152 A * | 7/1973 | Allen .................. | 206/299 |
| 3,780,857 A | 12/1973 | Rosano et al. | |
| 3,783,862 A | 1/1974 | Schrading et al. | |
| 4,099,614 A | 7/1978 | Heissenberger | |
| 4,342,392 A * | 8/1982 | Cox .................. | 206/438 |
| 4,515,270 A * | 5/1985 | Alvarado .................. | 206/438 |
| 4,564,107 A | 1/1986 | Heitzenröder et al. | |
| 5,244,718 A * | 9/1993 | Taylor et al. .................. | 442/208 |
| 5,635,134 A | 6/1997 | Bourne et al. | |
| 6,045,035 A * | 4/2000 | Murakami et al. .................. | 229/84 |
| 6,159,067 A * | 12/2000 | Willis et al. .................. | 446/207 |
| 7,172,107 B2 * | 2/2007 | Kranz .................. | 229/68.1 |
| 7,726,547 B2 * | 6/2010 | Tachikawa et al. .................. | 229/68.1 |
| 7,922,983 B2 | 4/2011 | Prokash et al. | |
| 8,261,963 B2 | 9/2012 | Gaynor et al. | |
| 2001/0036519 A1 | 11/2001 | Bayer | |
| 2005/0163654 A1 | 7/2005 | Stecklein et al. | |
| 2006/0144911 A1* | 7/2006 | Sierra-Gomez et al. .. | 229/123.1 |
| 2011/0033137 A1 | 2/2011 | Gaynor et al. | |

\* cited by examiner

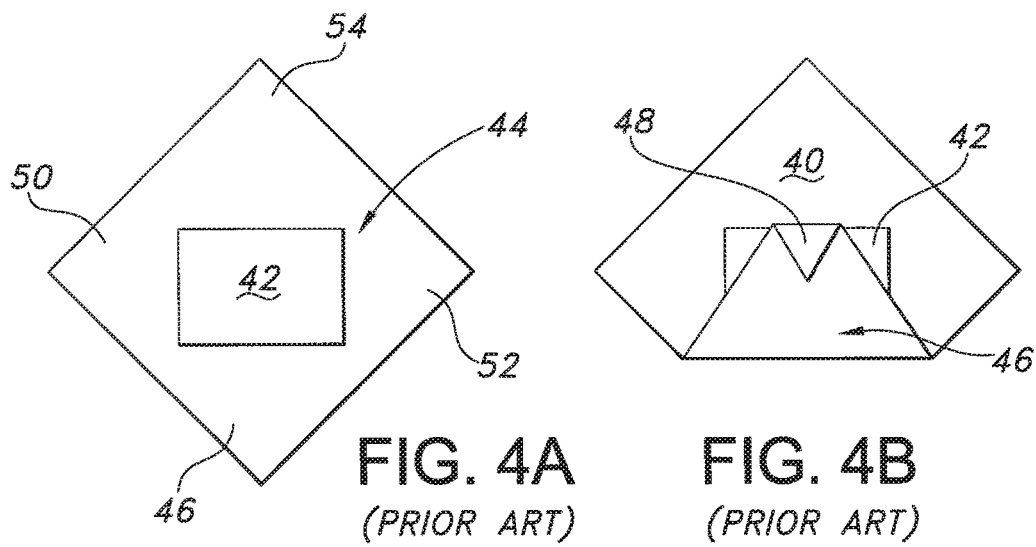
FIG. 4A
(PRIOR ART)
FIG. 4B
(PRIOR ART)
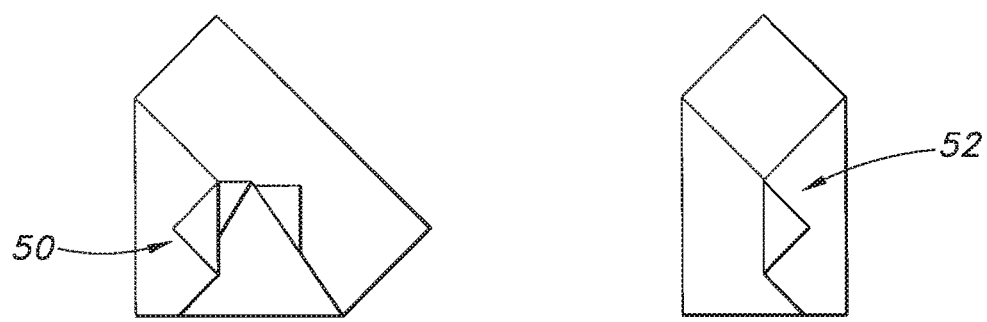
FIG. 4C
(PRIOR ART)
FIG. 4D
(PRIOR ART)
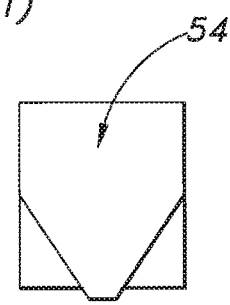
FIG. 4E
(PRIOR ART)

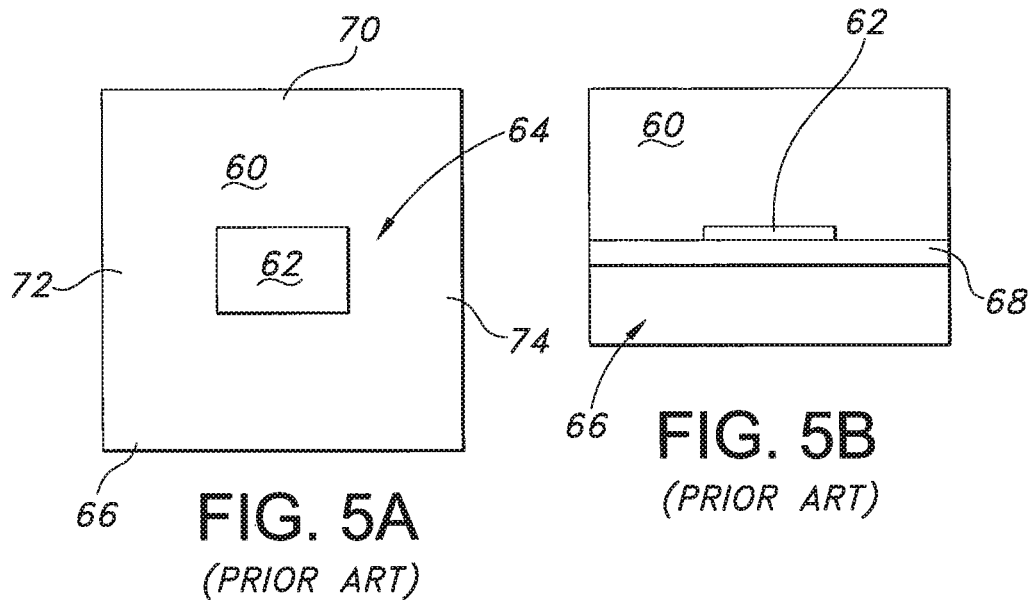
FIG. 5A (PRIOR ART)
FIG. 5B (PRIOR ART)
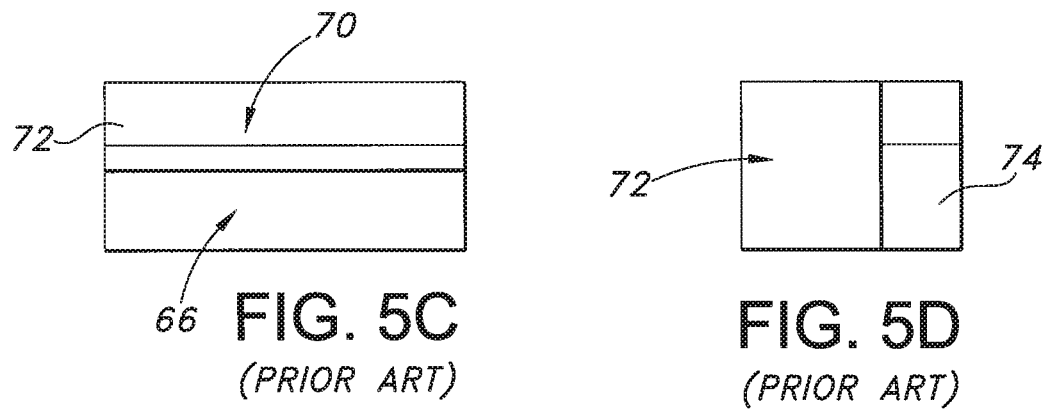
FIG. 5C (PRIOR ART)
FIG. 5D (PRIOR ART)
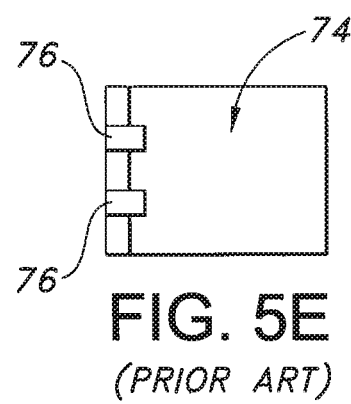
FIG. 5E (PRIOR ART)

FLEXIBLE MULTI-PANEL STERILIZATION ASSEMBLY WITH SIDE TABS

This application claims the benefit of priority from U.S. Provisional Application No. 61/541,655 filed on Sep. 30, 2011; U.S. Provisional Application No. 61/677,546 filed on Jul. 31, 2012; and from U.S. Provisional Application No. 61/678,751 filed on Aug. 2, 2012.

FIELD OF THE INVENTION

The present invention relates in general to disposable wraps used to contain content to be sterilized and store that content aseptically until use.

BACKGROUND OF THE INVENTION

A variety of products such as gowns, sheets, drapes, instruments, etc. which are required during surgery or other aseptic procedures, are used on a daily basis in the normal operation of hospitals, clinics and the like. Where such products are not pre-packaged in a sterile state, it is necessary for the hospital or clinic to sterilize them before use. Furthermore, where these products are not disposable, and are employed more than once, it is necessary that they be cleaned and otherwise prepared for subsequent use. Prior to such use, however, it is essential that such products be sterilized.

Due to the volume of materials involved, it is often necessary to sterilize and store these products for later use. Accordingly, there has been developed a procedure where such products, after cleaning, laundering and the like, are wrapped in suitable barrier fabric and then sterilized and stored for subsequent use. Such fabric is typically cut into predetermined rectangular shapes and sold as sterilization wraps.

Traditional wrapping of a sterilization tray or similar articles in a conventional disposable sterilization wrap often involves a large amount of redundant material as excess corners and overlapping plies are gathered, folded, and secured together at the top of the sterilization tray.

Conventional disposable sterilization wrap is a flat, featureless sheet of material that may occasionally contain one or more additional layers of material for strength or absorbency. This flat, featureless configuration provides no information or guidance to a person wrapping an article with the flat sheet of material on how to wrap an article.

Conventional disposable sterilization wrap is frequently made of inexpensive, relatively impermeable material such as, for example, paper and the like. The properties of these materials have generally influenced folding techniques and wrapping configurations to ensure the sterility of the wrapped tray or article.

For example, U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, U.S. Patent Application Publication No. 2001/0036519 by Robert T. Bayer discloses a two ply sterilization wrap that is formed of a single sheet of sterilization wrap material which is folded to form two similarly sized, superposed panels that are bonded to each other. As yet another example, U.S. Patent Application Publication No. 2005/0163654 by Stecklein, et al. discloses a sterilization wrap material that has a first main panel and a second panel that is smaller than the main panel. The second panel is superposed and bonded to the central portion of the main panel such that it is contained entirely within the main panel to reinforce the main panel and/or provide additional absorbency.

Generally speaking, in these and other examples, articles or content to be sterilized, e.g. trays with surgical instruments and/or supplies, singular instruments, absorbents, basins, etc., are centered on large sheets of conventional disposable sterilization wrap and the uncovered portions of the sterilization wrap are folded around the articles to create large expanses of overlapping materials using one or two standard fold techniques. These conventional techniques and the resulting fold configurations require manipulating excess amount of materials during the wrapping and unwrapping process. Additionally the use of these fold techniques provide for touch points or grip locations of the sterilization wrap material for subsequent unfolding. It takes experience and a certain level of skill to wrap a tray or similar article quickly and reliably. Because of scheduling and cost pressures, medical equipment needed for some procedures may require immediate turnaround and must be processed, sterilized and available for use within hours of its use in a previous procedure. As turnaround times continue to compress, there is a corresponding increase in the need to wrap an article even more quickly while ensuring the integrity of the fold configuration of the sterilization wrap (the wrapping) around the sterilized article. There is also a corresponding increase in the need to quickly unwrap a sterilized article while preserving the sterility of the sterilized article.

Large sheets of conventional disposable sterilization wrap in combination with standard fold techniques do provide an advantage during unwrapping of an item after sterilization, particularly when the sterilization wrap is formed from a material that may stiffen or take a set during the sterilization process. For example, when sterilization wrap composed of nonwoven material made from certain thermoplastic polymers are used in an extended or enhanced steam or heat sterilization process, the nonwoven material may take on a set or an "imprint" of the shape of the wrapped article or tray. During unwrapping of the article or tray, imprinted creases, folds or other deformations must be overcome during unfolding so the sterilization wrap can lay flat. If the sterilization wrap does not lie flat, it is possible for unfolded portions of the sterilization wrap to fold back up towards the sterilized article or tray while other portions of the wrap are being unfolded. This would compromise the sterility of the article. The large expanses of material and the rectangular shape of the sheets in combination with standard folding techniques generally keep the sterilization wrap from folding back onto itself during unwrapping. However, the use of large sheets of conventional disposable sterilization wrap with standard fold techniques provides large expanses of overlapping materials and multiple folds which require using and manipulating excessive amounts of material during the wrapping and unwrapping process, adding difficulty that slows the wrapping and unwrapping process, and creating waste.

When large sheets of conventional sterilization wrap are reduced in size, the reduction in material amplifies the problem of unfolded portions of the sterilization wrap folding back up towards the sterilized article or tray while other portions of the wrap are being unfolded. Moreover, this problem can also be amplified by altering the geometry of the sheet of sterilization wrap so the sheet is less square (e.g., in order to reduce the amount of material in the sheet).

Regardless of the size of conventional sterilization wrap, during unwrapping the sterilization wrap material must be grasped to unfold the overlapping expanses.

Accordingly, there is an unmet need for an easy to use assembly, package or system that reduces the amount of sterilization wrap material needed for the sterile processing of an instrument tray or article and eliminates the need to grasp the sterilization wrap material to unfold wrap. There is also an unmet need for an easy to use assembly, package or system that reduces the amount of sterilization fabric and simplifies the task of unwrapping a sterilized instrument tray or article while reducing or avoiding the likelihood that the sterilization fabric will fold back onto itself during unwrapping. The need is particularly apparent for an assembly, package or system that reduces the amount of sterilization fabric, that can be used in an extended or enhanced steam or heat sterilization process, and that simplifies the task of unwrapping a sterilized instrument tray or article while reducing or avoiding the likelihood that the sterilization fabric will fold back onto itself during unwrapping.

BRIEF SUMMARY OF THE INVENTION

The problems described above are addressed by the present invention which encompasses a flexible multi-panel sterilization assembly. The flexible multi-panel sterilization assembly (sterilization assembly) includes a barrier panel composed of a permeable sheet material having barrier properties, side tabs that include grip portions for folding or unfolding the barrier panel; and a fold protection panel.

The barrier panel includes: a first surface and a second opposing surface; a first end and a second end opposite the first end; a first edge and a third edge, each such edge being generally perpendicular to the first end; and a second edge that is away from or generally opposite the first end. Desirably, the barrier panel may have a fourth edge that is also located away from or generally opposite the first end such that the second edge and the fourth edge form an apex or vertex opposite the first end. More desirably, the barrier panel may have a fourth edge and a fifth edge to define a non-square or non-rectangular shape such that, for example, the fourth edge and a fifth edge generally converge toward the second edge such that the second end of the barrier panel is narrower than the first end of the barrier panel.

The barrier panel may have a maximum width that is the distance from the first edge to the third edge and a maximum length that is the distance from the first end to the second end. According to an aspect of the invention, the barrier panel has a midpoint which spans or runs between the first edge and the third edge to generally delineate the barrier panel into a content receiving region extending from a pre-determined fold line to the midpoint and a content covering region extending from the midpoint to the second end (e.g., the second edge). According to an aspect of the invention, the surface area of the content receiving region may be from about 25 percent to about 49 percent of the total surface area of the barrier panel. For example, the surface area of the content receiving region may be from about 35 percent to about 45 percent of the total surface area of the barrier panel.

The side tabs are located between the first end and the midpoint of the barrier panel and at or near (e.g., adjacent) the first and third edges of the barrier panel. These side tabs provide for grip portions for folding or unfolding the barrier panel. Desirably, the side tabs prevent the first and third edges of the barrier panel from folding back on itself during unfolding of the barrier panel, particularly after extended steam or heat sterilization. The side tabs may be one or more materials or layers of material selected from fibrous webs, textiles, films, cards, molded or extruded sheets and combinations thereof. For example, the side tabs may be a layer or layers of nonwoven material that extend from the barrier panel or may be joined to the barrier panel by adhesives, thermal bonding, ultrasonic bonding or other techniques. In an aspect of the invention, the side tabs are joined to the second surface of the barrier panel.

The multi-panel sterilization assembly further includes a fold protection panel in juxtaposed communication with the barrier panel. That is, the fold protection panel desirably extends from the barrier panel. If the fold protection panel is a separate piece of material, it is desirably immediately adjacent the first end of the barrier panel in side-by-side relationship. The fold protection panel may be the extension of a layer or layers of material(s) that form the barrier panel. The fold protection panel includes: a proximal end generally adjacent or adjoining the first end of the barrier panel; a distal end generally opposite the proximal end; and at least a first edge portion and a second edge portion extending from the proximal end toward the distal end. According to the present invention, the fold protection panel may have at least a third edge portion located at or along its distal end. One acceptable embodiment of the fold panel has multiple distinct straight edges so that each edge portion spatially represents the entire corresponding edge with respect to the proximal end; another acceptable embodiment of the fold panel has only one curved edge with a first edge portion and a second edge portion that extend from the proximal end toward the distal end and a third edge portion located at the distal end.

The fold protection panel may be configured so it has barrier properties. For example, the fold protection panel may be formed of the same material as the barrier panel. As another example, the fold protection panel may be formed of the same piece of material as the barrier panel.

In an aspect of the invention, the fold protection panel desirably has a maximum width that is the greatest distance from the first edge portion to the second edge portion and a maximum length that is the distance from the proximal end to the distal end, such that, after the barrier panel is folded at or near the barrier panel's midpoint so the barrier panel's second end is brought towards its first end and the side tab on the first edge and the side tab on the third edge are folded over the barrier panel towards or overlapping each other to form at least a partial enclose, the distal end of the fold protection panel is configured to cover at least the first edge and the third edge of the folded barrier panel.

The multi-panel sterilization assembly may optionally include a panel attachment means to join the side tabs to each other or to a portion of the content covering region after the barrier panel has been folded at or near its midpoint such that its second end is brought towards its first end. The panel attachment means may be adhesive tape, double-sided adhesive tape, cleavable release tapes, layered release tapes, cohesive materials, hook and loop fastening systems, mechanical fastening systems including, but not limited to, snaps, clips, magnets, catches, slots and tabs, and combinations thereof.

According to an aspect of the invention, the barrier panel further may further include indicia between the first edge and the third edge of the barrier panel. The indicia (which may be referred to as a "pre-determined fold line" or a "reference line") is desirably aligned generally parallel to the extremity of the first end of the barrier panel and is located away from the extremity in the direction toward the midpoint of the barrier panel. The indicia define an upper boundary of the content receiving region.

Barrier panel attachment means may be used to join the side tabs to each other or to a portion of the content covering region after the barrier panel has been folded at or near its midpoint such that its second end is brought near its first end. At least one barrier panel attachment means is desirably located on a portion of the side tab within the upper boundary of the content receiving region which may desirably by defined by the indicia.

In an aspect of the present invention, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments. The permeability of the sheet material of the barrier panel (or the barrier panel itself) may range from 25 to about 500 cubic feet per minute (CFM) as characterized in terms of Frazier permeability. For example, the permeability of the sheet material barrier panel may range from 25 to about 400 cubic feet per minute. As yet another example, the permeability of the sheet material of the barrier panel may range from 25 to about 300 cubic feet per minute. Alternatively and/or additionally, the permeability of the barrier panel may range from about 10 to about 30 cubic feet per minute when the barrier panel is composed of multiple plies or layers of a nonwoven laminate material.

The sterilization assembly may also include at least one pull tab. The pull tab provides a feature that aids the user to unwrap the sterilized article within the folded flexible multi-panel sterilization assembly aseptically. That is, during the unwrapping of an article, a person may use the pull tab to unfold the second end of the assembly and avoid reaching over the sterile field generally presented by unwrapping and spreading out the sterile content-contacting surface of the barrier panel. The pull tab may be unitary with the barrier panel or it may be attached to the barrier panel. Desirably, the pull tab is located at or near the second end of the barrier panel forming the content covering region and may desirably be located on the second surface of the barrier panel. The pull tab may be formed of the same material as the barrier panel, one or more different materials, or even the same piece of material as the barrier panel. Desirably, the pull tab or pull tabs provide for spaced apart pull locations. In an aspect of the invention, panel attachment means may attach to the content covering region between the spaced apart pull locations. For example, panel attachment means located on the side tabs may be configured to attach to the content covering region between the spaced apart pull locations.

The sterilization assembly may further include one or more discrete reinforcement elements. These elements are desirably in the content receiving region that define an area for receiving content to be sterilized. The reinforcement element(s) may include one or more layers of materials selected from fibrous webs, impermeable films, permeable or porous films, apertured films, foams, foils and combinations thereof. One or more of these reinforcement elements may extend beyond the second end of the barrier panel to provide a pull tab having spaced apart pull locations.

According to an aspect of the invention, the sterilization assembly may further include indicia or instructions on the sterilization assembly itself to inform the proper folding of the assembly into a package. Alternatively and/or additionally, the sterilization assembly may further include indicia or instructions on the sterilization assembly itself to inform the proper unfolding or unwrapping of the assembly after it has been folded into a package and sterilized.

In an aspect of the invention, there is provided a flexible multi-panel sterilization assembly that includes a barrier panel formed from a sheet of barrier material (e.g., barrier fabric) having at least one panel edge. The barrier panel is configured to be folded into side portions and an end portion to form a package around content to be sterilized. Side tabs generally extend diametrically from a portion of the barrier panel for sequentially positioning the side portions of the barrier panel in a folded configuration around content to be sterilized and provide grips for simultaneously unfolding the folded side portions of the barrier panel. The assembly further includes a fold protection panel extending from the barrier panel. The fold protection panel includes a proximal end generally adjacent the barrier panel and a distal end generally opposite the proximal end such that the distal end of the fold protection panel covers the one or more panel edges of the barrier panel after folding the side and end portions of the barrier panel. The fold protection panel may have barrier properties.

According to the invention, the side tabs may include panel attachment means. These may be selected from adhesive tape, double-sided adhesive tape, cohesive materials, hook and loop fastening systems, mechanical fastening systems, snaps, clips, magnets, catches, slots and tabs, and combinations thereof.

In an aspect of the invention, the sterilization assembly may further include a pull tab feature that comprises at least one pull tab and provides spaced apart pull locations. Panel attachment means that may be located on the side tabs may desirably be configured to attach to the barrier panel between the spaced apart pull locations. The sterilization assembly may further include discrete reinforcement elements on the barrier panel.

In yet another aspect of the invention, there is provided a flexible multi-panel sterilization assembly that includes at least one barrier panel composed of one or more thermoplastic materials compatible for recycling; and at least one separable component joined to the barrier panel, the separable component comprising at least one material that is less compatible for recycling with the thermoplastic materials of the barrier panel; such that the at least one separable component is joined to the barrier panel during use and separated from the barrier panel after use.

The at least one separable component may be side tabs extending diametrically from a portion of the barrier panel for sequentially positioning a first side portion and a second side portion of the barrier panel in a folded configuration around content to be sterilized and for providing grips for simultaneously unfolding the folded side portions of the barrier panel. Alternatively and/or additionally, the separable component may be at least one pull tab and two spaced apart pull locations. The side tabs may include barrier panel attachment means.

The barrier panel may include one or more sheets of barrier material having a first surface and a second opposed surface, a first end and a second end generally opposite the first end and a midpoint located between the first end and the second end, the midpoint generally delineating the barrier panel into a content receiving region extending from approximately the first end to the midpoint and a content covering region extending from the midpoint to approximately the second end; the sheet defining at least one panel edge, the barrier panel to fold into side portions and an end portion to form a package around content to be sterilized.

According to the invention, the sterilization assembly may also include a fold protection panel extending from the barrier panel, the fold protection panel consisting essentially of one or more thermoplastic materials compatible for recycling with the barrier panel. The fold protection panel may include a proximal end generally adjacent the barrier panel, a distal end generally opposite the proximal end; such that the distal end of the fold protection panel covers the one or more panel edges of the barrier panel after folding the side and end portions of the barrier panel.

In an aspect of the invention, the side tabs incorporating the barrier panel attachment means may be used to join the side tabs to each other or to a portion of the content covering region after the barrier panel has been folded at or near its midpoint such that its second end is brought near its first end. The barrier panel attachment means are desirably located on a portion of the side tab that the barrier panel attachment means is located or positioned within the upper boundary of the content receiving region. When the sterilization assembly includes side tabs and at least one pull tab and two spaced apart pull locations, the panel attachment means desirably attach to the content covering region between the spaced apart pull locations.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the Invention with reference to the accompanying drawing figures, in which like reference numerals denote similar structure and refer to like elements throughout, and in which:

FIGS. 4A to 4E are illustrations of an exemplary sequence of folding an exemplary prior art sterilization wrap system using a conventional envelope fold.

FIGS. 5A to 5E are illustrations of an exemplary sequence of folding an exemplary prior art sterilization wrap system using a conventional square fold.

FIG. 15 B is an illustration of an exemplary panel attachment means and a portion of the barrier panel to which it is attached during an exemplary shear test procedure.

FIG. 16 B is a side cross-sectional view illustrating detail from FIG. 16A showing features of an exemplary side panel and panel attachment means.

FIG. 16 D is a side cross-sectional view illustrating detail from FIG. 16B showing features of an exemplary side panel and panel attachment means during unfolding of an exemplary sterilization assembly.

DEFINITIONS

Figure 1:
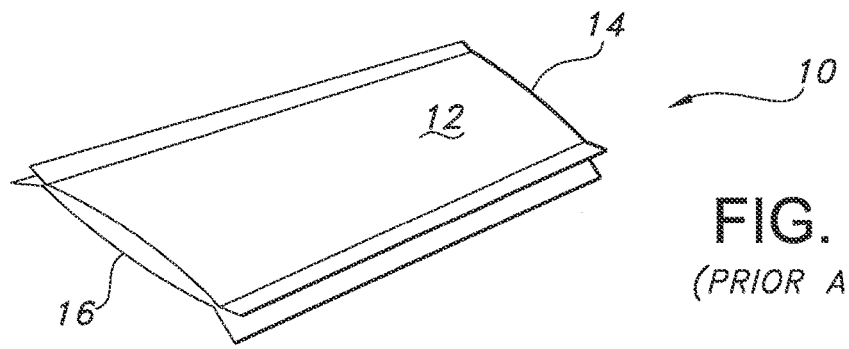
FIG. 1 is an illustration of an exemplary prior art sterilization wrap system.

As used herein, the term "basis weight" refers to the weight of a material per specified unit of surface area. This measure is usually associated with relatively thin, flat, sheet-like materials such as, for example, fabrics, films, papers, webs and the like. Basis weights of the materials discussed herein were determined essentially in accordance with Method 5041 of Federal Test Method Standard No. 191A. Basis weight may also be measured using test procedure ASTM D 3776-96 or TAPPI Test Method T-220. Basis weight is expressed in units of weight per unit of area (e.g., grams per square meter or ounces per square yard). These units may be abbreviated as "gsm" or "osy", respectively.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the term "machine direction" or MD means the length of a material or fabric in the direction in which it is produced. For example, the machine direction of a nonwoven web may be the planar dimension of the nonwoven web which is in the direction of travel of the forming surface onto which fibers and/or filaments are deposited during formation of the web. The term "cross machine direction" or CD means the direction generally perpendicular to the MD (which would be the width of fabric that has a machine direction along its length). For example, the cross-machine direction of a nonwoven web may be the planar dimension of the nonwoven web which is in the direction that is perpendicular to direction of travel of the forming surface onto which fibers and/or filaments are deposited during formation of the web.

As used herein, the term "meltblown" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, these fibers are carried by the high-velocity gas stream and are deposited on a collecting surface to form a web or fabric of randomly disbursed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, the term "multi-panel sterilization assembly" or "sterilization assembly" or "assembly" refers to a flexible article composed of fabric(s) and/or flexible material(s) that is wrapped around, folded around or otherwise encloses a non-sterile article or non-sterile content prior to sterilization. A sterilization assembly has multiple panels and/or sections providing specific physical properties, functional characteristics and/or structure that provide advantages for wrapping or folding, handling, strength, sterilization, storage after sterilization, and/or unwrapping or unfolding.

As used herein, the term "nonwoven" refers to a web or fabric that has a structure of individual fibers or filaments which are interlaid, but not in an identifiable repeating manner. Nonwovens have been, in the past, formed by a variety of processes known to those skilled in the art such as, for example, meltblowing, spunbonding and bonded carded web processes.

As used herein "point bonding" means bonding one or more layers of fabric at a plurality of discrete bond points. For example, thermal point bonding generally involves passing a fabric or web of fibers to be bonded between a heated roll assembly such as, for example, a heated calender roll and an anvil roll. The calender roll is usually patterned in some way so that the entire fabric is not bonded across its entire surface, and the anvil roll is usually smooth. As a result, various patterns for calender rolls have been developed for functional and/or aesthetic reasons. One example of a pattern has points and is the Hansen Pennings or "H&P" pattern with about a 30% bond area with about 200 bonds/square inch (31 bonds/square cm) as taught in U.S. Pat. No. 3,855,046 to Hansen and Pennings. Another example is shown in U.S. Design Pat. No. 239,566 to Vogt. Typically, the percent bonding area varies from around 5% to around 30% of the area of the fabric laminate web. Spot bonding holds the laminate layers together as well as imparts integrity to each individual layer by bonding filaments and/or fibers within each layer without destroying the breathability or hand of the fabric.

As used herein, the term "spunbond fabric" refers to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well-known spunbonding mechanisms. The production of spunbond nonwoven fabrics is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, "ultrasonic bonding" means a process performed, for example, by passing the fabric between a sonic horn and anvil roll as illustrated in U.S. Pat. No. 4,374,888 to Bornslaeger, the entire contents of which is incorporated herein by reference.

DETAILED DESCRIPTION OF INVENTION

In describing the various embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Referring now to FIG. 1, there is shown an exemplary conventional disposable sterilization wrap 10 having a multiple-ply configuration which is formed by joining one or more sheets 12 of sterilization wrap together to form two similarly sized, superposed panels 14 and 16 that allow convenient dual wrapping of an article. While one sheet may be folded back on itself to provide the multiple-ply configuration, two separate sheets are more typically used.

Figure 2:
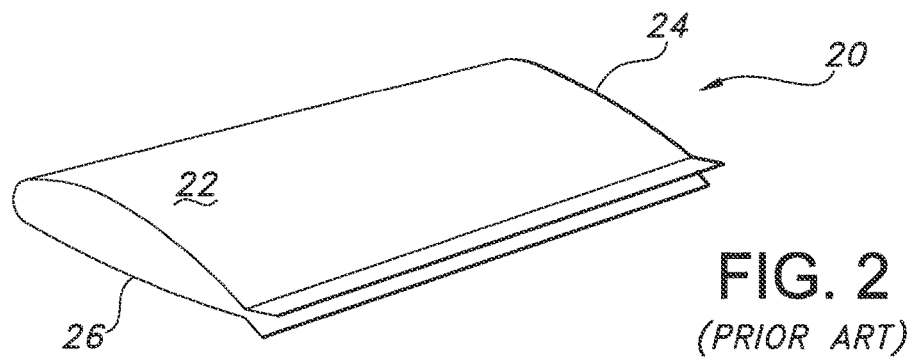
FIG. 2 is an illustration of an exemplary prior art sterilization wrap system.

FIG. 2 is an illustration of an exemplary conventional disposable sterilization wrap 20 as generally disclosed in U.S. Patent Application Publication No. 2001/0036519 by Robert T. Bayer. The conventional disposable sterilization wrap 20 is a two ply sterilization wrap formed of a single sheet 22 of sterilization wrap material which is folded to form two similarly sized, superposed panels 24 and 26 that are bonded to each other.

Figure 3:
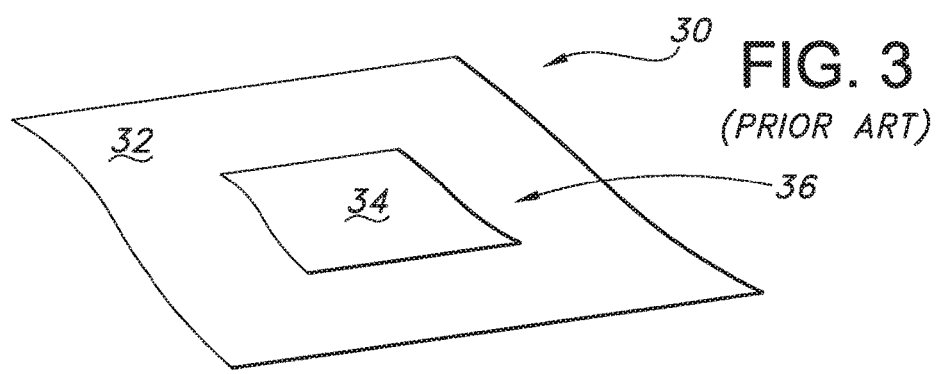
FIG. 3 is an illustration of an exemplary prior art sterilization wrap system.

FIG. 3 is an illustration of yet another example of a conventional disposable sterilization wrap 30 as generally disclosed in U.S. Patent Application Publication No. 2005/0163654 by Stecklein, et al. The conventional disposable sterilization wrap 30 has a first main panel 32 and a second panel 34 that is much smaller than the main panel 32. The second panel 34 is superposed and bonded to the central portion 36 of the main panel 32 to reinforce the main panel 32 and/or provide additional absorbency.

Generally speaking, in these and other examples, large sheets of conventional disposable sterilization wrap are typically used to create large expanses of overlapping materials using one or two standard fold techniques. These standard techniques and the resulting fold configurations require manipulating excess amount of materials during the wrapping and unwrapping process. It takes experience and a minimum level of skill to reliably wrap a tray or similar article quickly.

FIGS. 4A through 4E illustrate an exemplary sequence of steps in wrapping an article utilizing a conventional sterilization wrap. As illustrated in FIG. 4A, a square or generally rectangular wrap 40 is spread out flat and an article 42 to be wrapped is placed in a central region 44 of the wrap 40 in a generally diagonal relationship to the orientation of the wrap 40 in a pattern conventionally referred to as an envelope fold. Referring to FIG. 4B, a first end 46 of the wrap is folded up at the base of the article 42 and brought over the article 42. Generally speaking, the sterilization wrap must be sufficiently large in area to provide enough material to substantially cover the article in the initial fold. The first folded end 46 is back-folded to create a small tail 48. This sequence is time consuming, requires the worker to pay careful attention to the size of the tail, and is generally repeated for each of the remaining second end 50 and the third end 52. Again, the sterilization wrap must be sufficiently sized in area to provide enough material for the second end 50 and the third end 52 to substantially overlap such that the entire or substantially the entire second end 50 is covered by the third end 52. The fourth end 54 is folded over and taped to form a wrapped package.

FIGS. 5A through 5E illustrate another exemplary sequence of steps in wrapping an article utilizing a conventional sterilization wrap. As illustrated in FIG. 5A, a square or generally rectangular wrap 60 is spread out flat and an article 62 to be wrapped is placed in a central region 64 of the wrap 60 in a generally parallel relationship to the orientation of the wrap 60 in a pattern conventionally referred to as a square fold. Referring to FIG. 5B, a bottom end 66 of the wrap is folded up at the base of the article 62 and brought over the article 62. Generally speaking, the sterilization wrap must be sufficiently large in area to provide enough material to substantially cover the article in the initial fold. The folded bottom end 66 is back-folded to create a folded edge 68. This sequence is generally repeated for the remaining top end 70 and the left side end 72. Again, the sterilization wrap must be sufficiently sized in area to provide enough material for the top end 70 and the left side end 72 to substantially overlap such that the entire or substantially the entire bottom end 70 is covered by the left side end 72. The right side end 74 is folded over and taped 76 to form a wrapped package.

A typical sterilization tray with the dimensions of 10 inches (25.4 cm) by 20 inches (50.8 cm) by 5 inches tall (12.7 cm) typically requires a square piece of sterilization fabric having each side measuring 45 inches for wrapping and sterile processing. This large size piece is needed so that the corner of the fabric can be folded all the way across the top of the tray with some additional excess material so that the preparer of the tray feels confident that the contents are covered and that the piece of fabric will stay down and not spring back. Using a 45 inch square piece of fabric means that 2025 square inches of material (approximately 13,064 square centimeters) is being used to enclose a tray with a surface area of just 700 square inches (approximately 4,516 square centimeters). In other words, this traditional method requires almost three square inches of material to cover every square inch of a tray of surgical instruments.

The present invention encompasses a multi-panel sterilization assembly which addresses the problems generally described above and which also addresses a problem discovered when the dimensions of the sterilization fabric are reduced—namely unfolded portions of the sterilization fabric can partially re-fold or fold back on itself during unfolding of other portions of the sterilization assembly. An exemplary multi-panel sterilization assembly 100 is illustrated in FIG. 6.

The multi-panel sterilization assembly includes a barrier panel 102 composed of a permeable sheet material 104 having barrier properties (e.g., a barrier fabric), panel attachment means 106 (not shown in FIG. 6) for securing the barrier panel 102 into a package; and a fold protection panel 108. Generally speaking, the "barrier panel" is the portion of a multi-panel sterilization assembly that is formed from a material that is sufficiently permeable to permit a sterilizing gas to pass through it to effect sterilization and has barrier properties sufficient maintain that content in an aseptic condition after sterilization. A barrier panel should also be sufficiently flexible or conformable to that it is configured to receive and subsequently enfold or enclose content to be sterilized thereby forming a package. Generally speaking, the barrier panel may be a barrier fabric. The "fold protection panel" is the portion of a multi-panel sterilization assembly that is formed from a material covers and protects at least a portion of the folded edges of the barrier panel. The fold protection panel is the last panel or part of the multi-panel sterilization assembly that is folded or wrapped around the package (formed by the barrier panel around content to be sterilized) and is the first part of the multi-panel sterilization assembly that is unfolded or unwrapped. The barrier panel and fold protection panel are each desirably made of a material that provides the required properties yet is so inexpensive that is can be economically disposed of or recycled after a single use. Exemplary materials are polyolefin based nonwoven materials. As noted previously, such inexpensive materials can take a set during heat or steam sterilization such that they have creases or folds that can resist unwrapping and urge portions of the barrier panel back towards a folded position that may compromise aseptic opening of the package.

The barrier panel includes: a first surface 110 and a second opposing surface 112; a first end 114 having an extremity or edge "E"; a second end 118 opposite the first end 114; a first edge 120 that is generally perpendicular to the first end 114; a second edge 122 that is generally opposite the first end 114; and a third edge 124 that is generally perpendicular to the first end 114. The barrier panel 102 may include indicia 116 that may be located towards the extremity "E", but within the first end 114 of the barrier panel. The barrier panel also has a midpoint "M" along the length "L" and extending between the first edge 120 and the third edge 124 or, in some embodiments, additional edges to generally delineate the barrier panel 102 into a content receiving region 130 extending from indicia 116 to the midpoint "M" and a content covering region 132 extending from the midpoint "M" to the second edge 122. Of course, it is contemplated that additional edges may be added or that edges may be curvilinear or may include curvilinear portions.

The indicia 116 may be aligned generally parallel to the edge or extremity "E" of the first end 114 of the barrier panel 102. The indicia 116 is desirably located on the first surface 110 away from the extremity "E" of first end 114 in a direction toward the midpoint "M" of the barrier panel to define an upper boundary of the content receiving region 130. This upper boundary may also be referred to as a "pre-determined fold line". Generally speaking, the indicia 116 (also called the pre-determined fold line) is offset from the extremity "E" of the first end 114—but it is contemplated that the indicia 116 may contact the extremity "E" if the either the indicia or the extremity "E" is non-linear. Just as the extremity "E" defines a boundary or transition between the barrier panel 102 and the fold protection panel 108, the indicia 116 identifies the desired upper boundary of the content receiving region 130 for placing the content to be sterilized within the first end 114 of the barrier panel 102. Placement of an article (content to be sterilized) along the indicia 116 offsets the article from the extremity "E" of the first end 114 in order to provide a sufficient amount of barrier panel to fully surround the article after folding is complete. The indicia 116 may be offset from the boundary or transition defined by extremity "E" between the barrier panel 102 and the fold protection panel 108 by about 0.5 inch (~13 mm) to about 10.5 inches (~270 mm). Desirably, the indicia 116 are offset from the boundary or transition boundary or transition defined by extremity "E" by at least about 1.5 inches (~38 mm).

The indicia may be in various forms. The indicia 116 may be in the form of a seam (or seams) such as, for example, a stitched seam, an ultrasonic bond seam, adhesive bond seam, thermo-mechanical bond seam (e.g., a bar seal seam) or combinations thereof, that results from joining layers or plies together to form the barrier panel and the fold protection panel—or the seam(s) may result from joining pieces together if the barrier and fold protection panels are discrete pieces. Alternatively and/or additionally, the indicia 116 may be in the form of printing, or by an imprint such as a thermo-mechanical bond line (e.g., bar seal line) or pattern or other marks, or identified by a visible crease or other suitable distinguishing feature. The indicia 116 may be an intermittent line and it may be provided directly on the barrier panel, it may be provided on only a portion or portions of the barrier panel, or it may be provided on one or more reinforcement elements or other features if such are present.

As noted above, an important feature of the indicia 116 is to help delineate where the content to be wrapped and ultimately sterilized should be placed. That is, content to be wrapped and sterilized should be placed adjacent only one side of the indicia. As discussed subsequently, other features of the present invention signal to a user which side of the indicia is the appropriate side to place content. Yet another feature of the indicia 116 is that it helps defines an additional boundary, reference line or limit for the user during the wrapping of content to be sterilized. That is, during wrapping, as part of the barrier panel (i.e., the second end 118) is brought over to cover the content to be sterilized, this part of the barrier panel should not be extended substantially across or beyond the indicia 116. In contrast to conventional sterilization wrap systems where the content is placed at the center of the sterilization barrier, the multi-panel sterilization assembly requires placement of the content from the indicia 116 and towards the midpoint "M" rather than near the edge or extremity "E" of the first end 114 of the barrier panel. This is initially counterintuitive for users and is quite different from conventional sterilization wrap systems.

While the barrier panel 102 of FIG. 6 is generally shown as having a square shape, the barrier panel 102 may be rectangular or may desirably have additional edges to define a non-square or non-rectangular shape. Portions of the edges may be arcuate or may otherwise be non-linear. Alternatively and/or additionally, the first edge 120 and the third edge 124 may converge or diverge so the edges are not parallel, thereby defining a barrier panel 102 having a more trapezoidal shape. It is also contemplated that other combinations of opposite edges may converge or diverge.

Figure 7A:
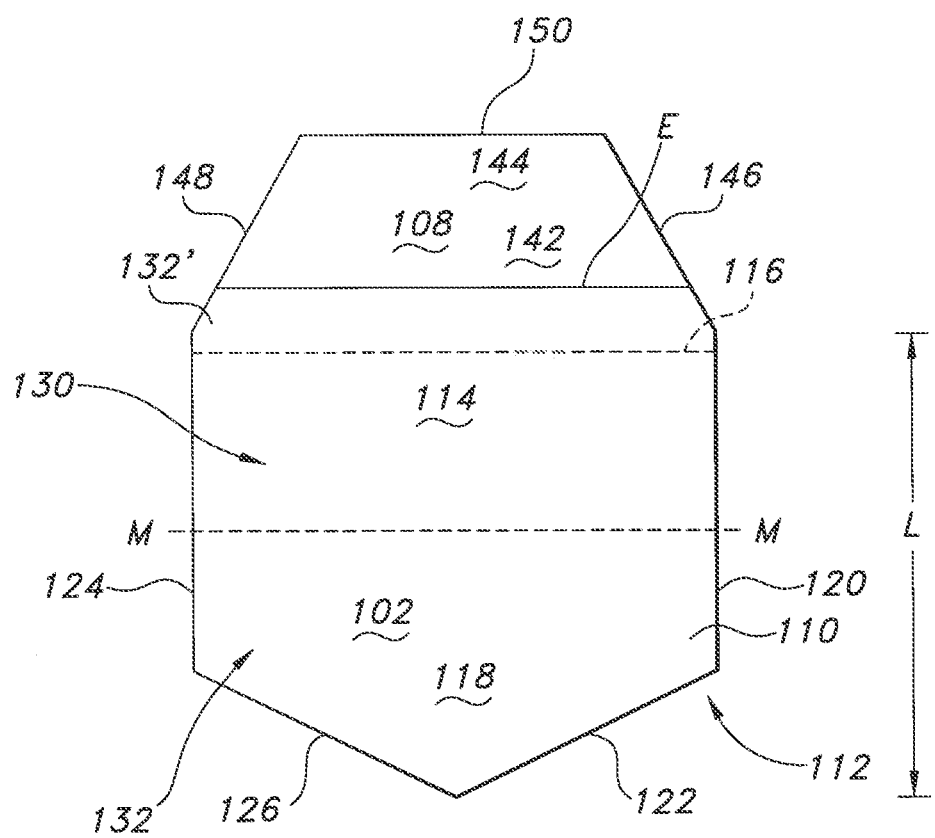
FIG. 7A is a top view illustration of an exemplary flexible multi-panel sterilization assembly including side tabs (not shown in the top view).
Figure 7B:
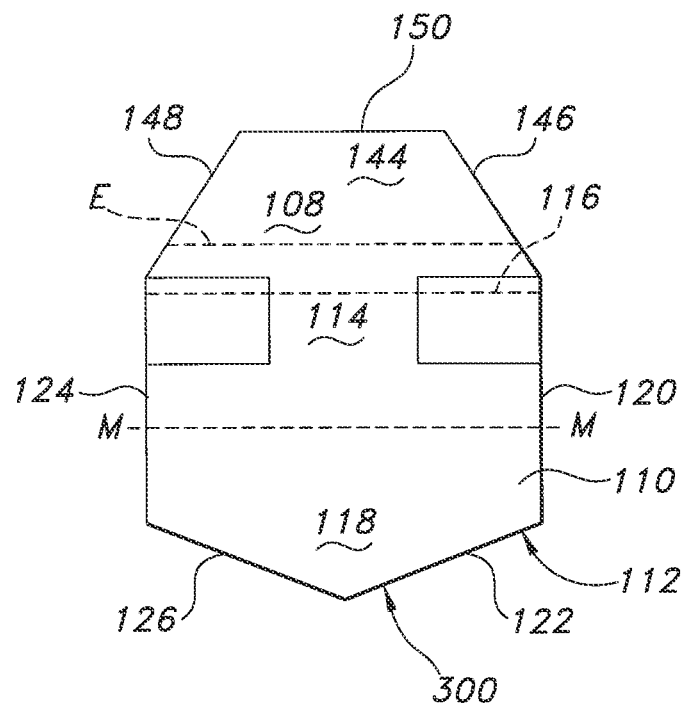
FIG. 7B is a bottom view illustration of an exemplary flexible multi-panel sterilization assembly including side tabs.
Figure 7C:
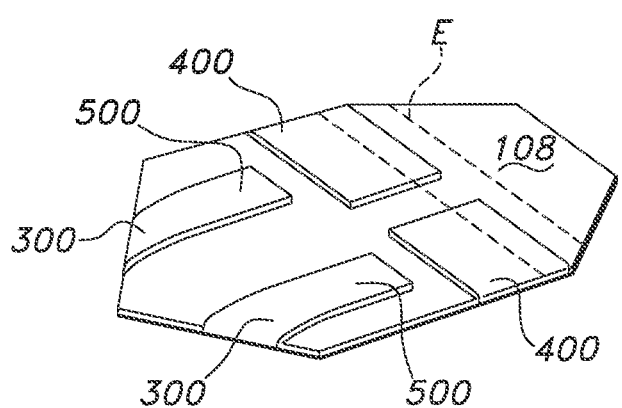
FIG. 7C is a bottom perspective view illustration of an exemplary flexible multi-panel sterilization assembly including side tabs and pull tabs with spaced apart pull locations.

For example and referring to FIG. 7A, the barrier panel may have a fourth edge 126 to define a non-square or non-rectangular shape. In such an exemplary configuration, the two edges 122 and 126 are generally opposite the pre-determined fold line 116 such that the second edge 122 and the fourth edge 126 form an apex or vertex. Thus, the barrier panel 102 may have a first surface 110 and a second opposing surface 112; a first end 114 having an edge or extremity "E" and that contains a pre-determined fold line 116 (also called indicia 116); a second end 118 opposite the first end 114; a first edge 120 that is generally perpendicular to the pre-determined fold line 116; a second edge 122 that is generally opposite the pre-determined fold line 116; a third edge 124 that is generally perpendicular to the pre-determined fold line; and a fourth edge 126 located between the second edge 122 and the third edge 124.

Figure 8A:
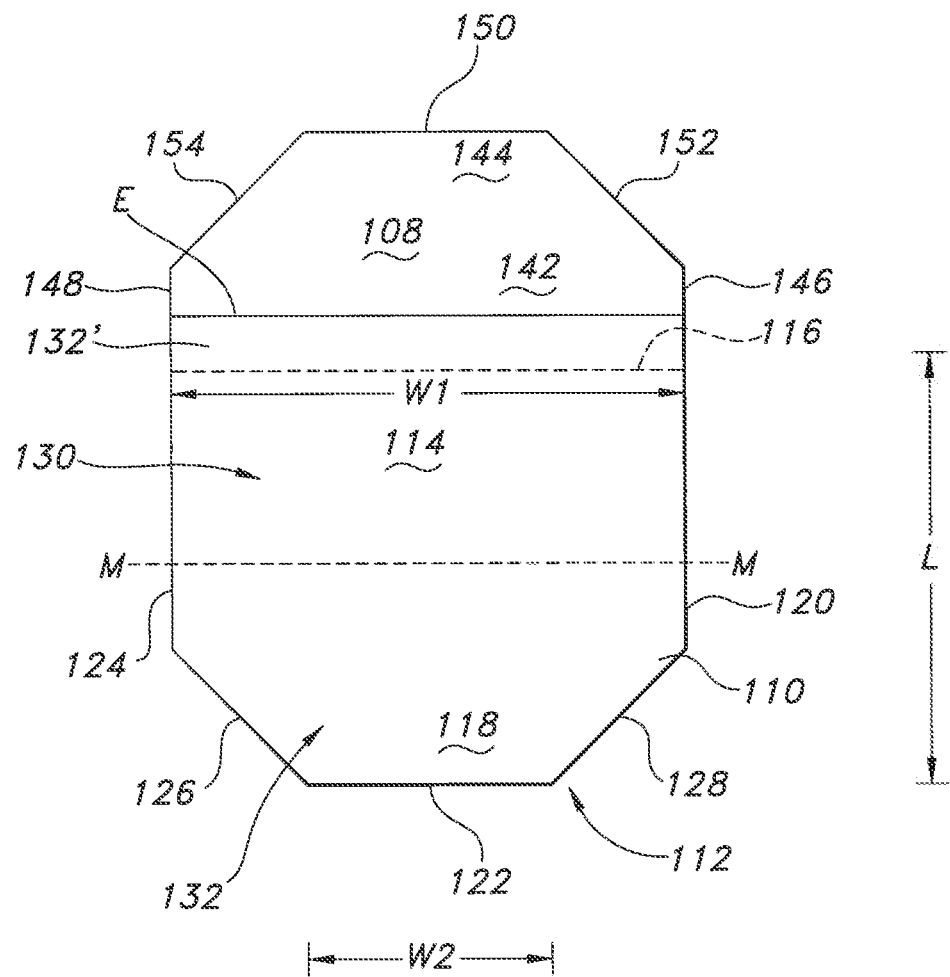
FIG. 8A is a top view illustration of an exemplary flexible multi-panel sterilization assembly including side tabs (not shown in the top view).
Figure 8B:
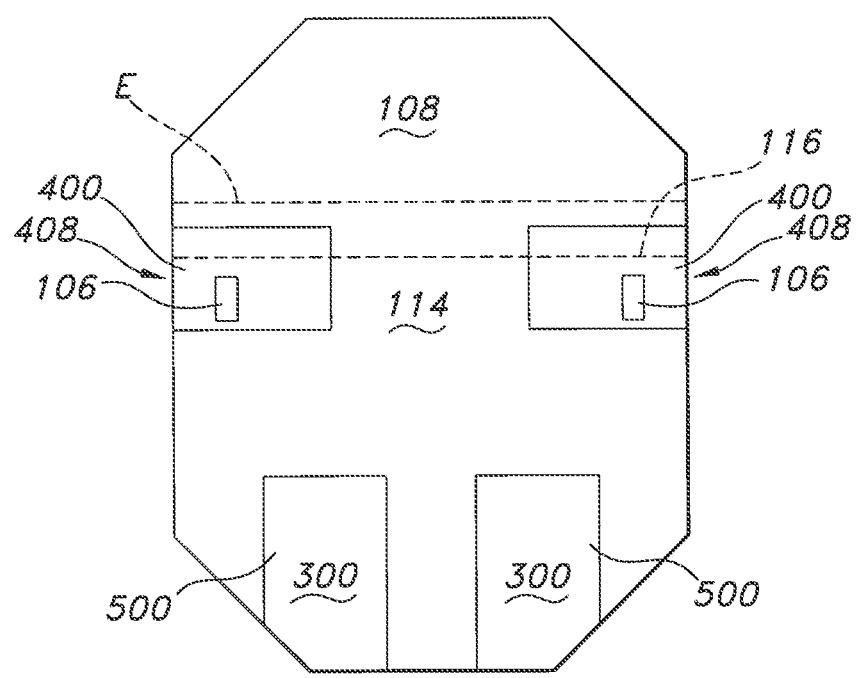
FIG. 8B is a bottom view illustration of an exemplary flexible multi-panel sterilization assembly including side tabs and pull tabs with spaced apart pull locations.

Referring to FIGS. 8A and 8B, the barrier panel 102 may have a fourth edge 126 and a fifth edge 128 to define a non-square or non-rectangular shape such that, for example, the fourth edge 126 and a fifth edge 128 generally converge toward the second edge 226 such that the second end 118 of the barrier panel is narrower than the first end 114 of the barrier panel. Thus, the barrier panel 102 may have a first surface 110 and a second opposing surface 112; a first end 114 having an edge or extremity "E" and that contains a pre-determined fold line 116; a second end 118 opposite the first end 114; a first edge 120 that is generally perpendicular to the pre-determined fold line; a second edge 122 that is generally parallel to the pre-determined fold line 116; a third edge 124 that is generally perpendicular to the pre-determined fold line 116; a fourth edge 126 located between the second edge 122 and the third edge 124; and, a fifth edge 128 located between the first edge 120 and the second edge 122. The barrier panel has a first width "W1" that is the distance from the first edge 120 to the third edge 124 in the first end 114 (e.g., preferably measured along the pre-determined fold line 116) and a second width "W2" that is the distance along the second edge 122 from the fourth edge 126 to the fifth edge 128 (e.g., preferably measured between the locations where the fourth edge 126 and the fifth edge 128 meet the second edge 122. The barrier panel also has an overall length that is the distance from the extremity "E" of the first end 114 to the extremity of the second end (e.g., at the second edge 122). In addition, the barrier panel has a length "L" from the pre-determined fold line 116 (or indicia 116) to the extremity of the second end 118 (e.g., at the second edge 122). An approximate midpoint "M" is located along this length "L" and is oriented from the first edge 120 and the third edge 124 or, in some embodiments, the fourth edge 126 and the fifth edge 128 to generally delineate the barrier panel 102 into a content receiving region 130 extending from the indicia 116 (also referred to as the pre-determined fold line 116) to the midpoint "M" and a content covering region 132 extending from the midpoint "M" to the second edge 122. Of course, it is contemplated that additional edges may be added or that edges may be curvilinear or may include curvilinear portions.

Figure 6A:
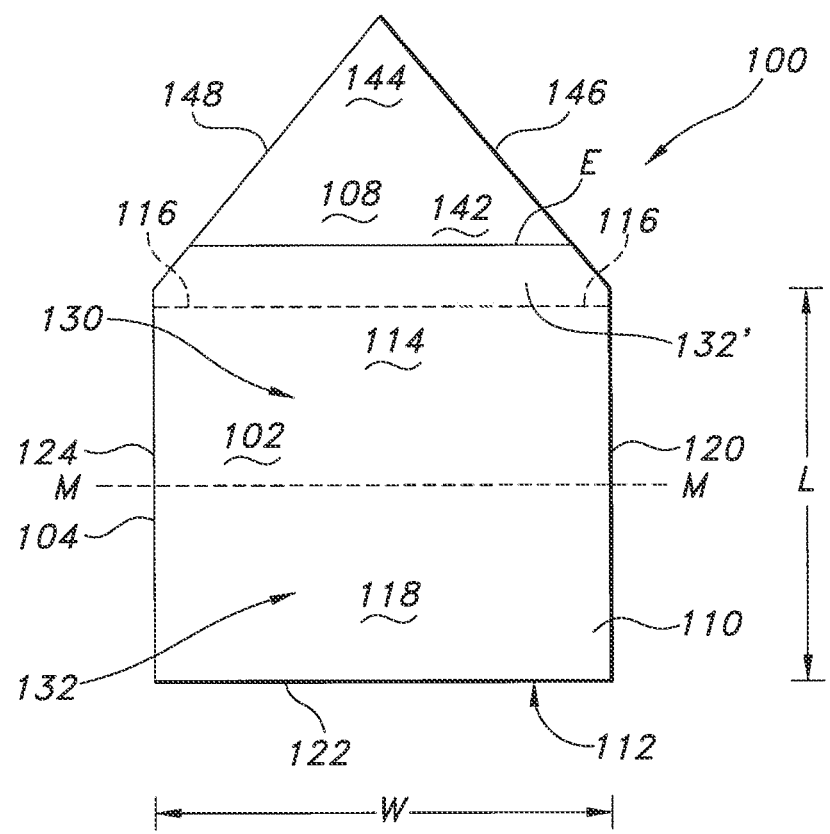
FIG. 6A is a top view illustration of an exemplary flexible multi-panel sterilization assembly including side tabs (not shown in the top view).
Figure 6B:
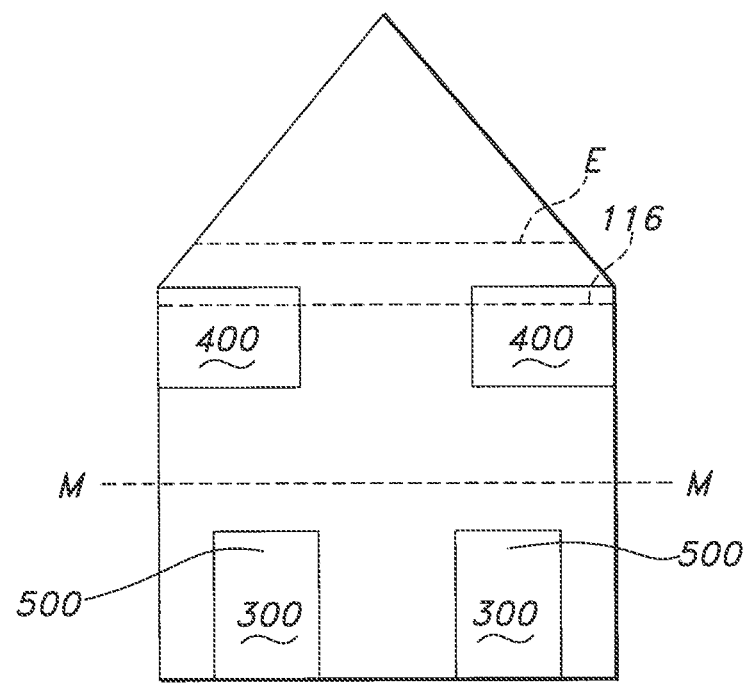
FIG. 6B is a bottom view illustration of an exemplary flexible multi-panel sterilization assembly including side tabs and pull tabs with spaced apart pull locations.

Referring again to FIG. 6A, the barrier panel 102 may have a width "W" that is the distance from the first edge 120 to the third edge 124 and an overall length that is the distance from the extremity "E" of first end 114 to the extremity of the second end 118 (e.g., at the second edge 122). The barrier panel also has a length "L" from the pre-determined fold line 116 (or indicia 116) to the extremity of the second end 118 (e.g., at the second edge 122). An approximate midpoint "M" along this length "L" is oriented from the first edge 120 and the third edge 124 to generally delineate the barrier panel 102 into a content receiving region 130 extending from the pre-determined fold line 116 to the midpoint "M" and a content covering region 132 extending from the midpoint "M" to the second edge 122. Generally speaking the content receiving region is the portion of the barrier panel onto which a tray or other content to be sterilized is initially placed. Unlike conventional sterilization wrap in which a tray or content to be sterilized is placed in the central portion of the barrier material that forms the sterilization wrap, the content receiving region is between the indicia 116 (also referred to as the pre-determined fold line 116) and the midpoint "M" of the barrier panel. This asymmetric placement on the barrier panel is not intuitive. Content covering regions are the portions of barrier panels that are folded up and over contents after contents have been placed on the content receiving regions. Referring to FIGS. 6A, 7A and 8A, when the extremity "E" of the first end 114 of the barrier panel does not coincide with the indicia 116 (also referred to as the pre-determined fold line 116), an additional content covering region 132' may be present between the indicia 116 and the "E" of the first end 114 of the barrier panel. That is, in another aspect of the invention, the content covering region of the barrier panel 102 also includes the region of the barrier panel 132' located between the pre-determined fold line 116 (also called the indicia 116) and the extremity "E" of the first end 114 that defines a boundary or transition between the barrier panel 102 and the fold protection panel 108.

In an aspect of the invention, the barrier panel of the various illustrated configurations may have a width of from about 12 inches (~30 cm) to about 50 inches (~127 cm). Desirably, the barrier panel may have a width of from about 18 inches (~46 cm) to about 40 inches (~102 cm). Even more desirably, the barrier panel may have a width of from about 20 inches (~51 cm) to about 48 inches (~122 cm). The barrier panel may have a length of from about 7 inches (~18 cm) to about 70 inches (~178 cm). Desirably, the barrier panel may have a length of from about 14 inches (~36 cm) to about 70 inches (~178 cm). Even more desirably, the barrier panel may have a length of from about 14 inches (~36 cm) to about 51 inches (~130 cm).

According to an aspect of the invention, the surface area of the content receiving region 130 may be from about 25 percent to about 49 percent of the total surface area of the barrier panel 102. For example, the surface area of the content receiving region 130 may be from about 35 percent to about 45 percent of the total surface area of the barrier panel 102. This is important because the content covering region or regions of the barrier panel should be larger to provide additional surface area to properly cover the content.

Figure 8C:
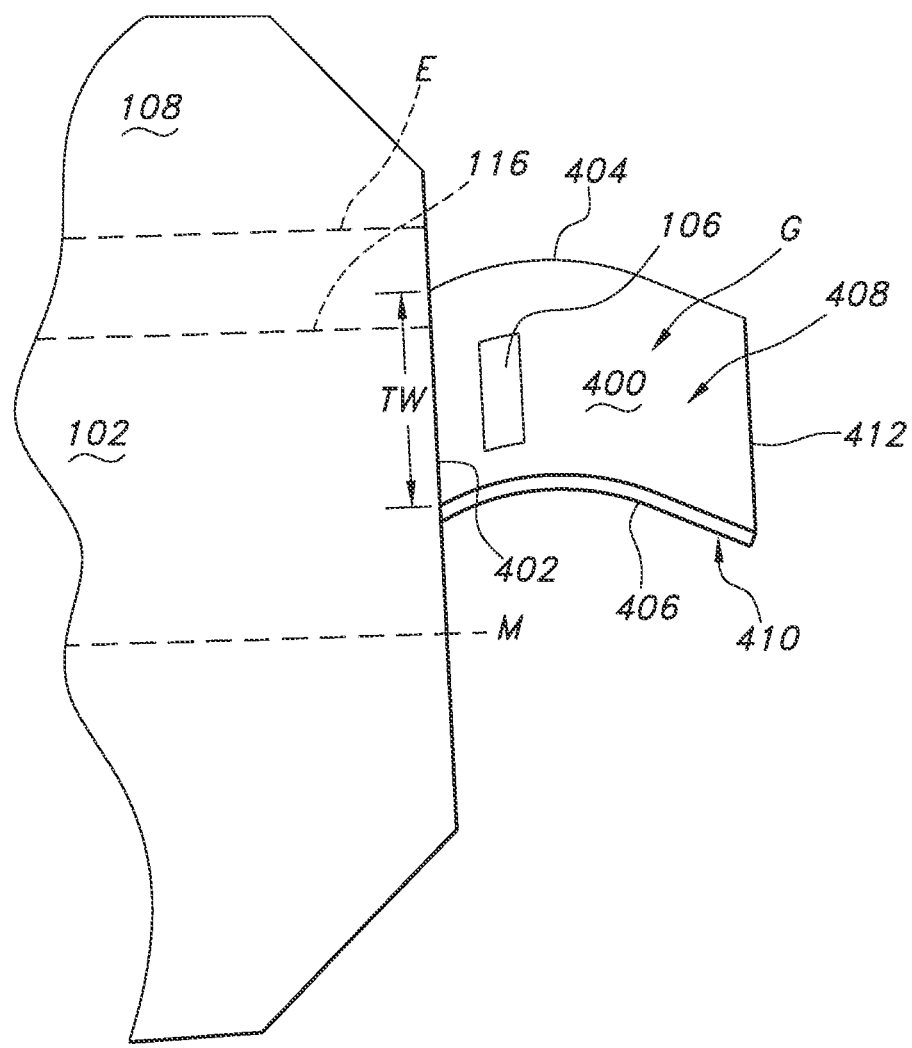
FIG. 8C is an illustration of a detail of an exemplary side tab located on a flexible multi-panel sterilization assembly.
Figure 8D:
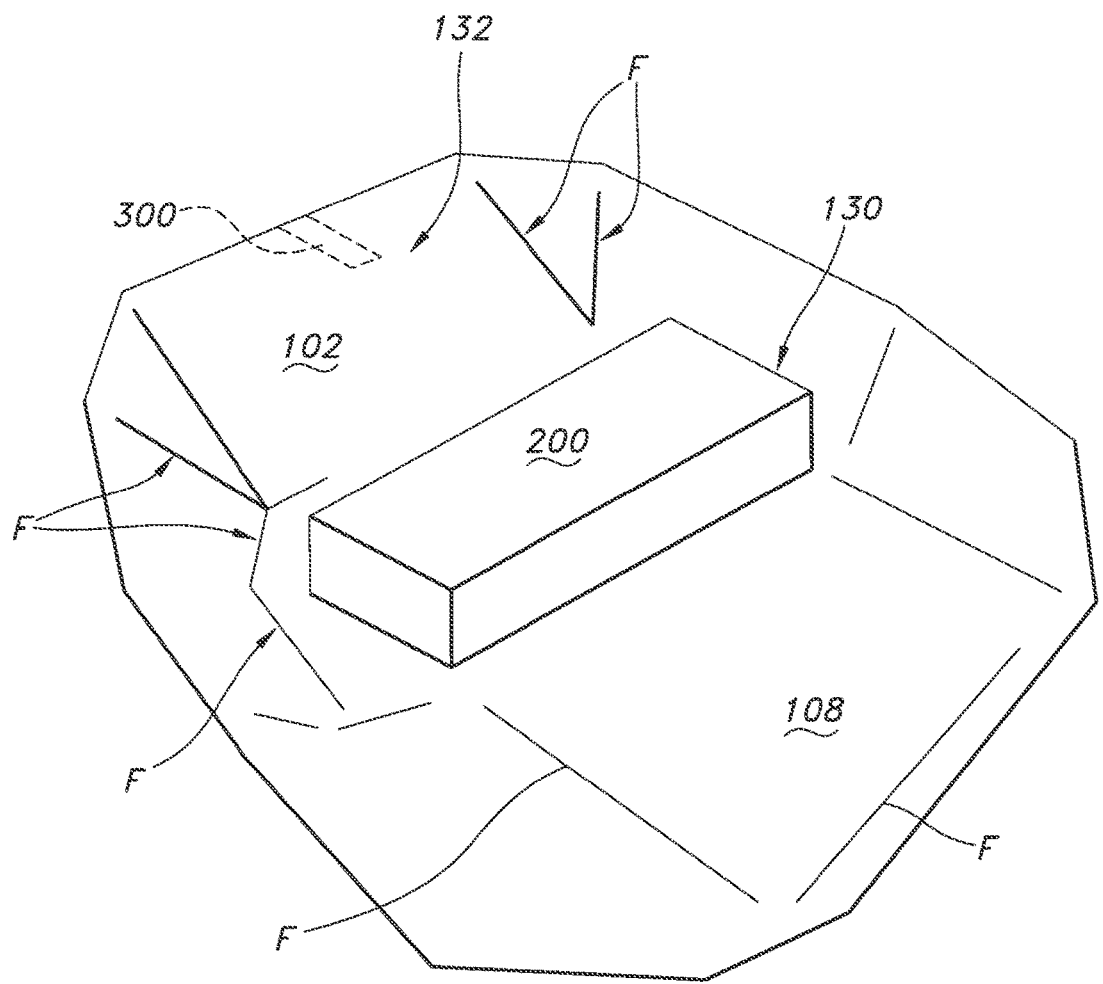
FIG. 8D is in illustration of sterilization assembly during unfolding highlighting imprinted creases, folds and other deformations that prevent portions of the assembly from laying flat during unfolding.
Figure 8E:
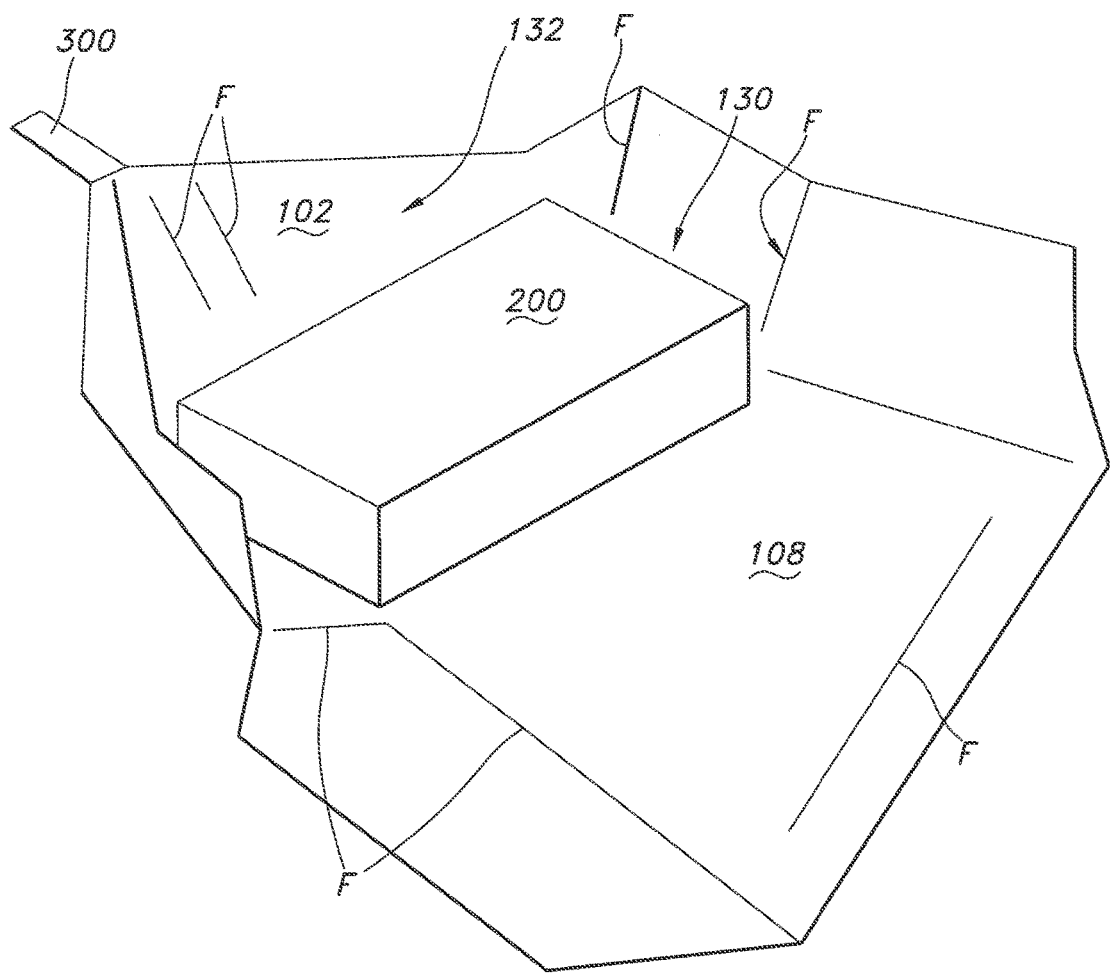
FIG. 8E is in illustration of sterilization assembly during unfolding highlighting imprinted creases, folds and other deformations that cause partially unfolded sides of the assembly to fold back up towards the sterilized article or tray while other portions of the assembly are being unfolded.

An important part of the multi-panel sterilization assembly of the present invention is the side tabs. These side tabs provide grip locations for folding and unfolding the barrier panel. Importantly, these side tabs help prevent unfolded portions of the barrier panel from folding back towards the sterilized contents during unfolding of other portions of the sterilization assembly, particularly after enhanced steam or heat sterilization. In the absence of these side tabs, the side edges of the barrier panel may fold back up towards or even onto the sterilized content. Referring now to FIGS. 8D and 8E, when a sterilization wrap or sterilization assembly composed of a material made from certain thermoplastic polymers are used in steam or heat sterilization processes, the material may set or "imprint" the shape of the wrapped article or tray. During unwrapping of the article or tray 200, these imprinted creases, folds or other deformations identified as "F" in FIG. 8D must be overcome during unfolding so the sterilization assembly can lay substantially flat. If the sterilization assembly does not lie substantially flat, it is possible for previously unfolded sides of the sterilization assembly to fold back up towards the sterilized article or tray while other portions of the assembly are being unfolded. This phenomenon can compromise the sterility of the article or tray 200. Ordinarily, one would seek to make the material of the sterilization assembly or wrap softer, more flexible and compliant so it would fold and unfold easily and be able to lay flat during unwrapping/unfolding after sterilization. However, making the material softer or more flexible creates additional expense and may compromise the strength of the material. Alternatively, one might seek to reinforce the material and make it stiffer or add more material such as, for example, a wide strip along the edge of the barrier panel. However, it has been found that adding more material frequently tends to strengthen or enhance the tendency of the imprinted crease, fold or other deformation to fold back up. It is believed that adding more material at the "F" fold, crease or deformation locations allows more material to "heat set" thus increasing the resistance to unfolding. It is also thought that a very large amount of material is required to provide sufficient weight to begin to counterbalance the resistance to unfolding and that such a large amount of material is uneconomical to employ and would create difficulties during manufacture and use. The additional weight of material also lowers the breathability of the wrap.

It was unexpectedly discovered that adding side tabs and/or the pull tab having spaced apart pull locations to the sterilization assembly significantly reduces or eliminates the likelihood of previously unfolded sides of the sterilization wrap folding back up over the sterilized article or tray while other portions of the wrap are being unfolded. Joining the side tabs and/or the pull tab(s) to the barrier panel at sites that span the locations where the imprinted crease, fold or other deformation occur was found to be particularly effective. In addition, the side tabs provide for even easier and faster folding and unfolding of the sides of the sterilization assembly.

Referring to FIGS. 6 to 8C, the barrier panel 102 includes side tabs 400 located at or adjacent the first edge 120 and the third edge 124 of the barrier panel. These side tabs 400 help prevent the first and third edges of the barrier panel from folding back on itself during unfolding of the sterilization assembly, particularly after extended steam or heat sterilization. The side tabs 400 can be located at or adjacent the first and third edges (120 and 124, respectively) of the content covering region 132 of the barrier panel 102. Desirably, the bulk of a side tab 400 is located between the extremity "E" of the first end and the midpoint of the barrier panel and at or near the first edge and the third edge such that the tab 400 spans the indicia 116 (also called pre-determined fold line 116). Generally speaking, the side tabs 400 may be located on the second opposing surface 112 of the barrier panel 102 as illustrated in FIGS. 6B, 7B, 7C, 7D and 8B. Alternatively and/or additionally, side tabs 400 may be located on the first surface 110 of the barrier panel 102. For example, the side tabs 400 may be configured such that a portion of the side tab is attached to the first surface 110 and another portion is attached to the second opposed surface 112.

In an aspect of the present invention, the sterilization assembly includes at least one pull tab 300 (or pull tab system 300) that provides spaced apart pull locations 500. Generally speaking, the pull tab system 300 may be located on the second opposing surface 112 of the barrier panel 102 as illustrated in FIGS. 6B, 7C, 7D and 8B. Alternatively and/or additionally, the pull tab system 300 may be partially located on the first surface 110 of the barrier panel 102. For example, the pull tab system 300 may be configured such that a portion of the pull tab is attached to the first surface 110 and another portion is attached to the second opposed surface 112.

In another aspect of the invention, the side tabs may be attached to the side panel such that the side tabs may be readily separated from the barrier panel after use (i.e., after sterilization and unfolding of the sterilization assembly to reveal the sterilized content). Alternatively and/or additionally, the attachment of the pull tabs may be such that the pull tabs may be readily separated from the barrier panel after use (i.e., after sterilization and unfolding of the sterilization assembly to reveal the sterilized content). This may be particularly advantageous where components such as panel attachments means are present on the side tabs and portions of the panel attachments means are made of a material that is incompatible for recycling with the material(s) that form other portions of the sterilization assembly. It is contemplated that the side tabs may be unitary or integral to the barrier panel (e.g., they may be formed from a single piece of material. In such case, the side tabs may include a frangible portion such that the side tabs may be readily separated from the barrier panel.

The side tabs (and/or the pull tab(s)) may include one or more layers of materials selected from fibrous webs, impermeable films, permeable or porous films, apertured films, foams and combinations thereof. For example, fibrous webs may include those that are woven and nonwoven. Woven webs may include natural or synthetic materials or blends of the same. As examples, natural materials could be weaves of cotton yarn, and synthetic materials could be weaves of polypropylene, polyester, or nylon yarn and the like. Nonwoven webs may include, for example, spunbond, meltblown, carded webs, wet formed or airlaid webs, hydroentangled fabric, or laminates of the same (e.g., spunbond/meltblown/spunbond). Such nonwoven webs may also include natural or synthetic materials or blends of the same. The side tabs may include one or more layers of material selected from permeable or impermeable films or laminates of the same. Permeable films may be apertured or be microporous. Apertured films may be obtained through mechanical aperturing, vacuum aperturing, or other commercially available techniques. Microporous films and other similar films may be produced as generally described at, for example, U.S. Pat. No. 5,695,868; U.S. Pat. No. 5,698,481; U.S. Pat. No. 5,855,999; and U.S. Pat. No. 6,277,479; the contents of which are incorporated herein by reference. Impermeable films can be monolayer or coextruded and can be comprised of film materials including, for example, polyethylenes, polypropylenes, copolymers thereof, vinyls, metal foils, and the like. It should also be noted said films may also be laminated with fibrous webs, described above.

For example, the side tabs (and/or the pull tab(s)) may be a layer or layers of nonwoven material that is joined to the barrier panel by adhesives, thermal bonding, ultrasonic bonding or other techniques or combinations of techniques. For example, each side tab may be a layer of nonwoven material such as, for example, a laminate of two layers of spunbond fabric sandwiching a layer of meltblown fabric (commonly referred to as "SMS" material). Each layer may extend directly from or generally adjacent the respective first and third edges of the barrier panel. For example, the side tab may extend from at or adjacent the edge to a few inches inward from the edge.

Each side tab may be joined to the barrier panel over only a portion of its surface that directly contacts the barrier panel. Alternatively, each side tab may be joined to the barrier panel over the entire surface of the side tab that directly contacts the barrier panel. For example, the side tab may be joined to the barrier panel utilizing a spray of adhesive, a slot-coat application of adhesive, swirl pattern of adhesive over that entire contacting surface—or over only a portion of that contacting surface and particularly to attach the portions of the side tabs that are inward from the edges of the barrier panel. The portions of the side tabs that are at or immediately adjacent from the edges of the barrier panel may be attached utilizing adhesives as described above or by ultrasonic bonding, thermal bonding, pressure bonding or other techniques. When adhesives are utilized, the adhesive should withstand sterilization conditions. It is contemplated that an adhesive which can add to the weight and/or stiffness of the side tab would be desirable.

Figure 7D:
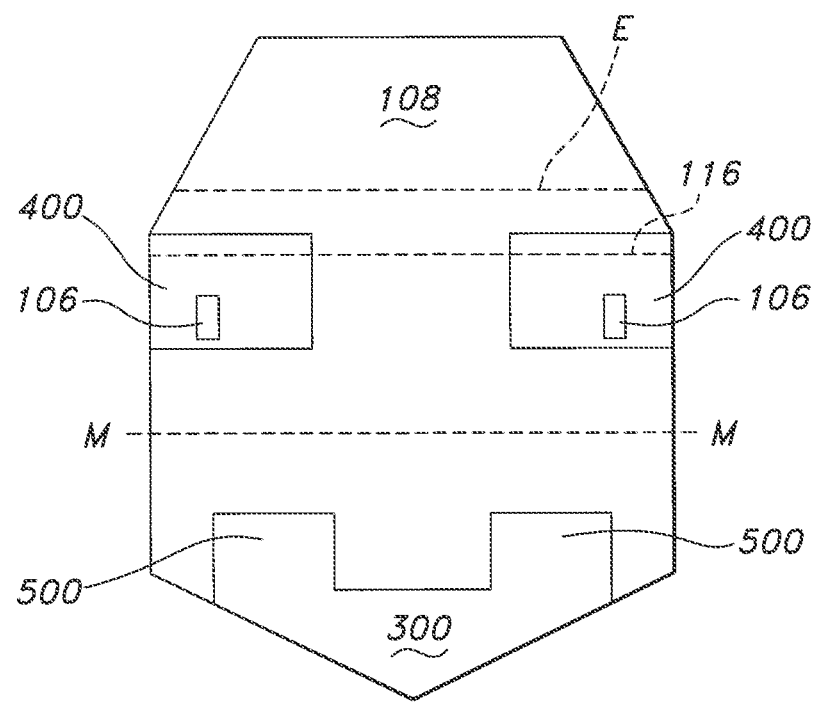
FIG. 7D is a bottom view illustration of an exemplary flexible multi-panel sterilization assembly including side tabs and a pull tab with spaced apart pull locations.

The multi-panel sterilization assembly 100 may include a panel attachment means 106. For those embodiments where the side tabs have rectangular shapes the panel attachment means may desirably be located on a side tab 400 as generally illustrated in FIG. 8C. Each side tab 400 may include a proximal tab end 402 generally adjacent the respective first edge or third edge of the barrier panel, a first tab edge 404 generally perpendicular to the proximal tab end and at least a second tab edge 406 such that the first tab edge 404 and the second tab edge 406 define a tab width "TW" at the proximal tab end 402. The side tab may also have a distal tab end 412 opposite the proximal tab end 402. According to an aspect of the invention, the tab width "TW" should extend a distance from a first location at or near the first end of the barrier panel (e.g., a location at or above the indicia 116 and at or below where the barrier panel 102 transitions to the fold protection panel 108—identified in FIG. 8C as extremity "E") to at least a second location below the indicia 116 and within the content receiving region (e.g., to a second location on the barrier panel 102 that is located below the indicia 116 in the direction toward the midpoint "M" of the barrier panel). The panel attachment means 106 is desirably located on a first tab surface 408 generally near the proximal tab end 402 (i.e., near the first edge 120 and/or or the third edge 124 of the barrier panel). The panel attachment means should be located below the indicia 116 (the "pre-determined fold line") as generally illustrated in FIGS. 7D, 8B and 8C.

Alternatively and/or additionally, the panel attachment means 106 may be located at or adjacent the first edge 120 and the third edge 124 of the barrier panel. That is, the panel attachment means may be located directly on the first surface 110 of the barrier panel 102. In such a configuration, the panel attachment means 106 should be located below the indicia 116 (the "pre-determined fold line").

While the inventors should not be held to a particular theory of operation, it is believed that having the tab width "TW" of the side tab at the proximal tab end 402 span the indicia 116 (also called the pre-determined fold line 116) which is a location where an imprinted crease, fold or other deformation occurs as a result of sterilization, the side tab is able to distribute forces during opening of the package to effectively and reliably prevent unfolded sides of the sterilization assembly from folding back up over the sterilized article or tray while other portions of the wrap are being unfolded.

The panel attachment means may be one large element or a number of discrete elements. Exemplary panel attachment means include, but are not limited to, adhesive tape, double-sided adhesive tape, cleavable release tapes, layered release tapes, cohesive materials, hook and loop fastening systems, mechanical fastening systems including, but not limited to, snaps, clips, magnets, catches, slots and tabs, and combinations thereof.

For example, the panel attachment means may be one or more lengths of adhesive tape having at least an end or portion that is stitched, ultrasonically bonded, thermo-mechanically bonded or adhered or adhesively bonded to the barrier panel. Desirably, the panel attachment means is a barrier panel attachment means located on the side tabs that is used to join one or more edges of the barrier panel that are folded around content to be sterilized. It has been found that barrier panel attachment means may be a double sided tape having the same or different levels of adhesive or tack strength of adhesive on each side. Alternatively and/or additionally, the panel attachment means may have a double sided tape structure in which the central layer sandwiched by the adhesive is a splittable or separable material such as a splittable paper, splittable laminate, splittable foam, cleavable paper, cleavable release structure, cleavable foam or other cleavable or separable laminate. Exemplary splittable or cleavable materials are disclosed at, for example, U.S. Pat. No. 5,702,555 issued to Caudal et al. on Dec. 30, 1997; U.S. Pat. No. 4,310,127 issued to Frye on Jan. 12, 1982; U.S. Pat. No. 3,675,844 issued to Sorrell on Jul. 11, 1972; and U.S. Pat. No. 2,205,956 issued to Humphner on Jun. 25, 1940; the contents of which are incorporated by reference.

Suitable panel attachment means 106 that include or incorporate adhesive tape may be in the form of an adhesive fastening tab or tape closure system such as the various types frequently used on diapers, incontinent garments and similar products. An exemplary tape closure system may be found at, for example, U.S. Pat. No. 4,410,325 issued to Lare on Oct. 18, 1983; the contents of which are incorporated by reference. This system utilizes an adhesive closure system (referred to herein as a "closure system") that is folded back on itself and which has a first end or portion that is attached to the article (e.g., one part of a garment). During use, the closure system is unfolded to reveal an exposed adhesive surface at least at a second end or portion of the closure system which is then adhered to a different part of the article (e.g., a second part of the garment) to secure the two parts of the garment in the desired configuration. Generally speaking, the closure system is desirably used on the side tabs 400 that are located at the first edge 120 and the third edge 124 (although it may be used directly on the barrier panel 102). The first end of the panel attachment means 106 (in the form of the closure system) would be secured on the first tab surface 408 or would be secured at or near the distal tab end 412 of the side tab 400 and the second end of the panel attachment means 106 would be folded back onto the first end. During use, the panel attachment means 106 would be unfolded to reveal an exposed adhesive surface or surfaces at least at the second end of the panel attachment means 106. The exposed adhesive surface(s) of the panel attachment means on the side tabs 400 at first edge 120 and/or third edge 124 of the barrier panel would be used to secure those portions of the barrier panel to each other and/or to other portions of the barrier panel after the barrier panel is folded about content to be sterilized.

It is contemplated that an optional attachment zone may be utilized. In embodiments that utilize adhesive or cohesive materials for the panel attachment means, an attachment zone may be an applied film, a more securely bonded portion of a nonwoven fabric, a separate piece of a material, a coating or the like that provides a suitable surface for the adhesive to bond securely so the folded barrier panel does not "pop" open or release when it should not do so. The attachment zone may be configured to signal to a user the appropriate location or locations to secure the panel attachment means. In such configuration, the attachment zone may be combined with or may incorporate indicia such as color, texture, alphanumeric characters or the like to direct a user. More importantly, the attachment zone can be configured to provide a suitable surface such that the force required to release the panel attachment means 106 is carefully controlled to preserve aseptic opening, avoid tearing or shredding of the barrier fabric, provide a satisfactory level of resistance to sheer forces, and/or provide a satisfactory or controlled level of resistance to peel forces.

Another exemplary tape closure system may be found at, for example, U.S. Pat. No. 4,585,450 issued to Rosch et al. on Apr. 29, 1986; the contents of which are incorporated by reference. This system utilizes an adhesive closure system (referred to herein as a "closure system") that includes a secondary tape element and a primary tape element. The closure system has a first end or portion that is attached to the article (e.g., one portion of a garment). The second end or portion contains the secondary tape element and primary tape element. During use, an adhesive surface of the primary tape element is exposed. The adhesive surface of the primary tape element is then adhered to a different part of the article (e.g., a second part of the garment) to secure the two parts of the garment in the desired configuration. An adhesive bond between the primary tape element and the secondary tape element has less strength than the adhesive bond between the primary tape element and the second part of the garment or article such that the bond between the primary tape element and secondary tape element may be reliably separated, repeatedly if necessary.

Generally speaking, the closure system is desirably used on the side tabs 400 that are located at the first edge 120 and the third edge 124 (although it may be used directly on the barrier panel 102). The first end or first side of the panel attachment means 106 (in the form of the closure system) would be secured on the first tab surface 408 or would be secured at or near the distal tab end 412 of the side tab 400 and the second end or the second side of the panel attachment means 106 would be folded back onto the first end or otherwise covered by a release element. During use, the primary tape element of the panel attachment means 106 (in the form of the closure system) would be unfolded or uncovered to reveal an exposed adhesive surface(s) at least at the second end or second side of the panel attachment means 106. The exposed adhesive surface(s) of the panel attachment means on the side tabs 400 at first edge 120 and/or third edge 124 of the barrier panel would be used to secure those portions of the barrier panel to each other and/or to other portions of the barrier panel after the barrier panel is folded about content to be sterilized. In such a configuration, the adhesive bond between the primary tape element and the secondary tape element has less strength than the adhesive bond between the primary tape element and the portion of the side tab to which it is adhered such that the bond between the primary tape element and secondary tape element may be reliably separated, repeatedly if necessary. In some respects, the primary tape element may function as an attachment zone. That is, after the primary tape element is adhered to the barrier panel to secure the barrier panel in a folded configuration, the primary tape element may provide a suitable surface such that the force required to overcome the adhesive bond between the primary tape element and the secondary tape element is carefully controlled to preserve aseptic opening, avoid tearing or shredding of the barrier fabric, provide a satisfactory level of resistance to sheer forces, and/or provide a satisfactory or controlled level of resistance to peel forces. In another aspect, the attachment zone as describe previously or in the form of the primary tape element may be used to allow a worker to re-open the wrapped barrier panel prior to inspect contents prior to sterilization and then re-attach the panel attachment means without having to destroy the multi-panel sterilization assembly.

As another example, the panel attachment means may be a hook fastener component from a hook and loop fastening system joined to the side tab (and/or to a portion of the barrier panel). It is contemplated that the barrier fabric itself may function as the loop component of a hook and loop fastening system such as hook and loop fastenings systems available as VELCRO® brand fastener products from Velcro Industries B.V. Other exemplary hook systems may be used such as the hook system described in U.S. Pat. No. 5,315, 740 issued to Nestegard which relates to hooks having small dimensions so they engage low cost loop materials such as nonwoven webs.

It is contemplated that various elements or components of the panel attachment means, may be integrally formed, such as by molding, co-extrusion or the like, along with any associated substrate layer. For example, the individual hook elements may be integrally formed simultaneously with a hook base-layer by coextruding the base layer and hook elements from substantially the same polymer material.

The panel attachment means 106 may be a double sided tape having a length that is greater than its width. For example, the panel attachment means may be a double sided tape having a length that more than two times great than its width. As another example, the panel attachment means may be a double sided tape having a length that is four times great than its width to eight times greater than its width. Alternatively and/or additionally, the configuration of the panel attachment means may be a series of tape squares arranged along a dimension or within the dimensions of the side tab 400.

According to an aspect of the invention, the panel attachment means 106 may be located on the barrier panel or on the side tabs (or both) so that it is near the pre-determined fold line 116, but the panel attachment means 106 should avoid substantially spanning or crossing the pre-determined fold line 116. That is, the panel attachment means 106 should desirably avoid being in position such that it is creased or folded during folding of the multi-panel assembly into a package around an article. Desirably, the portion of the panel attachment means 106 closest to the pre-determined fold line 116 is about 3 inches or less away from the pre-determined fold line 116 in the direction toward the midpoint "M" of the barrier panel 102. More desirably, the portion of the panel attachment means 106 closest to the pre-determined fold line 116 is desirably from 1 inch to 3 inches from the pre-determined fold line 116. For example, the portion of the panel attachment means 106 closest to the pre-determined fold line 116 may be about 1 inch to about ½ inch from the pre-determined fold line 116.

Referring again to FIG. 6A, the fold protection panel 108 of the multi-panel sterilization assembly 100 is in juxtaposed communication with the barrier panel 102. That is, the fold protection panel 108 is in side-by-side relationship with or adjoins the barrier panel 102. Generally speaking, the fold protection panel 108 may be any suitable material but desirably is formed of a permeable sheet material. According to the invention, the fold protection panel includes a proximal end 142 generally adjacent the extremity "E" of the first end 114 of the barrier panel 102; a distal end 144 generally opposite the proximal end 142; and at least a first edge 146 and a second edge 148 extending from the proximal end 142 to the distal end 144. According to the present invention, the fold protection panel may have additional edges. For example and with reference to FIG. 7A, the fold protection panel may include at least a third edge 150 located at or along its distal end 144. As yet another example and referring now to FIG. 8A, the fold protection panel may include at least a third edge 150 located at or along its distal end 144 and a fourth edge 152 and a fifth edge 154.

Generally speaking, the fold protection panel may be a lightweight material such as a lightweight spunbond nonwoven material or a lightweight laminate of spunbond nonwoven material and meltblown nonwoven material. As such, the fold protection panel does not need to provide a higher level of barrier properties like the material that forms the barrier panel. The fold protection panel may be configured so it has barrier properties. For example, the fold protection panel may be formed of the same material as the barrier panel. It is contemplated that the fold protection panel may be a single layer of spunbond nonwoven material.

In an aspect of the invention, the fold protection panel desirably has a width that is the distance from the first edge to the second edge and a length that is the distance from the proximal end to the distal end. The fold protection panel may have a width of from about 12 inches (~30 cm) to about 50 inches (~127 cm). Desirably, the fold protection panel may have a width of from about 18 inches (~46 cm) to about 40 inches (~102 cm). Even more desirably, the fold protection panel may have a width of from about 20 inches (~51 cm) to about 30 inches (~76 cm). The fold protection panel may have a length of from about 6 inches (~15 cm) to about 30 inches (~76 cm). Desirably, the fold protection panel may have a length of from about 7 inches (~18 cm) to about 20 inches (~51 cm).

During use, panel attachment means 106 are used to securely position the barrier panel's first edge 120 and third edge 124 to a portion of the content covering region 132 after the barrier panel 102 has been folded at or near its midpoint "M" such that its second end 118 is brought near its first end 114. It is contemplated that in some embodiments, the panel attachment means 106 may be used to securely position the barrier panel's first edge 120 and third edge 124 to each other.

According to an aspect of the invention, it is important that the adhesive force or the engagement force at which the panel attachment means securely position the respective edges of the barrier panel to the content covering region or to the edges themselves should be sufficient to maintain the barrier panel around the content thereby forming a package that is robust and able to withstand normal handling before as well as after sterilization.

In exemplary arrangements, especially where there are sufficiently high levels of engagement shear force provided by the panel attachment means, the fastening engagement may provide a peel force value of not less than a minimum of about 5 grams-force (gmf) (about 0.012 lbs-force) between the panel attachment means and the other portion of the barrier panel that it secures together. Generally speaking, the peel force should not be more than about 500 gmf, and desirably is not more than about 400 gmf to further provide improved benefits. In further arrangements, the fastening engagement may provide a peel force value of between about 6 gmf and about 50 gmf to provide improved advantages. In desired configurations, the fastening engagement may provide a peel force value about between about 10 gmf and about 400 gmf between the panel attachment means and the other portion of the barrier panel that it secures together. More desirably, the peel force value may be between about 15 gmf and about 300 gmf. When the peel force is greater than about 500 gmf, there is difficulty opening/unwrapping the folded assembly containing sterilized contents in an aseptic manner.

The engagement force between the panel attachment means and the other portion of the barrier panel that it secures together may additionally provide a shear force value that is desirably greater than about 1330 gmf.

It should be readily appreciated that the adhesive force or the engagement force at which the panel attachment means securely position the respective edges of the barrier panel to the content covering region of the barrier panel or to the edges themselves should be less than the peel strength of the bond that is used to join the panel attachment means to the underlying barrier panel or component such as the side tabs during construction of the assembly. For example, the peel strength of the bond (e.g., adhesive, mechanical, thermomechanical, ultrasonic, etc.) that is used to join the panel attachment means to the side tabs during construction should be much greater than the detachment force for the panel attachment means from the barrier panel. For a panel attachment means having a dimension of about 4 inches by 1 inch (about 10 cm by 2.5 cm) the bond joining the panel attachment means to the side tab should have a peel strength of at least 100 gmf. Desirably, the peel strength of the bond that is used to join the panel attachment means to the side tabs during construction should be greater than about 400 gmf. For example, the peel strength may be more than 100 gmf/square inch, and may be more than 4,000 gmf/square inch. When the panel attachment means are located on or joined to the side tabs 400, it is important that the adhesive force or the engagement force at which the panel attachment means join the respective edges of the barrier panel to the content covering region of the barrier panel or to the edges themselves should be less than the strength of the bond between the side tabs and the barrier panel.

Figure 9A:
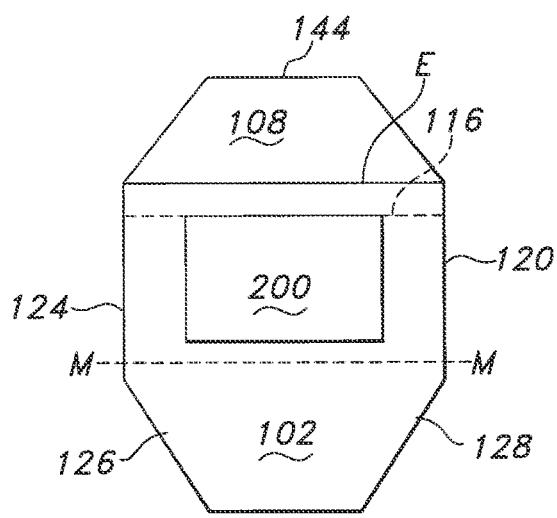
FIGS. 9A to 9G are illustrations of an exemplary sequence of folding an exemplary disposable flexible multi-panel sterilization assembly including side tabs and pull tabs having spaced apart pull locations.

Referring now to FIGS. 9A through 9G (and with additional reference to FIG. 8A), there is illustrated an example of a multi-panel sterilization assembly in an exemplary sequence of folding. FIG. 9A illustrates a multi-panel sterilization assembly 100 composed of barrier panel 102 which cooperates with the fold protection panel 108 and the panel attachment means 106 on the first surface 110 so the barrier panel 102 can be folded around the content 200 to form a package (such as the package 202 generally illustrated in FIGS. 9G and 10A). The barrier panel 102 is the portion of the flexible multi-panel sterilization assembly 100 that contacts and covers the content 202. The content 200 is placed in the content receiving 130.

Figure 9B:
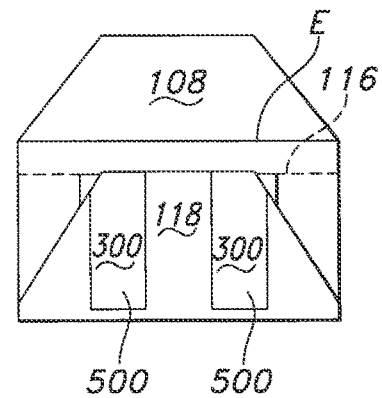

As generally illustrated in FIG. 9B, the second end 118 of the barrier panel 102 is folded up at the midpoint "M" and brought towards the first end 114 so the content covering region 132 of the barrier panel 102 extends over the content 200. As shown in FIG. 9B, the width of the barrier panel at the second end 118 is less than the width of the barrier panel at the first end 114. This is important when the panel attachment means 106 are located directly on the barrier panel (rather than being located on the side tabs 400) because it provides a configuration of the fourth edge 126 and the fifth edge 128 that allows access to the panel attachment means 106 after the second end 118 is brought up to the first end 114.

In some embodiments of the present invention, a pull tab system 300 and spaced apart pull locations 500 extend from the second end 118 so that the pull tab system 300 is positioned to be accessible during the final steps of unfolding or unwrapping a wrapped package. The pull tab system 300 desirably extends from or is joined to the second end 118 of the barrier panel on the second opposing surface 112 of the barrier panel 102. Referring briefly to FIG. 7D, there is shown a configuration in which the pull tab system 300 is a single tab that provides spaced apart pull locations 500. It is contemplated that the pull tab system 300 may be unitary or integral with the barrier panel. FIG. 7D also illustrates that pull tab system 300 is located on the second opposing surface 112 of the barrier panel 102. The distal end (i.e., the loose end) of the pull tab system 300 is desirably secured to the barrier panel with a light adhesive or an adhesive tab or sticker such that the pull tab system 300 does not flop around during wrapping and is in an appropriate position during unwrapping.

Figure 9C:
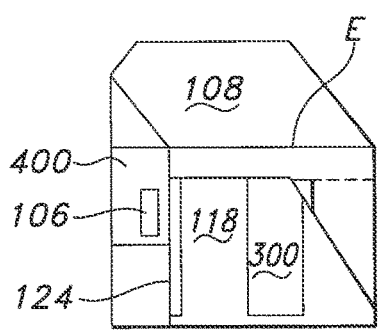

Referring now to FIG. 9C, that illustration shows that the third edge 124 of the barrier panel 102 is folded over the second end 118 (after the second end 118 is brought up to the first end 114). While not necessarily shown to scale, the third edge 124 of the barrier panel 102 after folding need not extend very far toward the middle of the assembly.

Figure 9D:
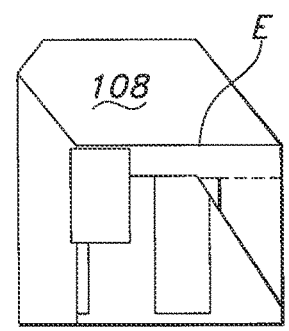
Figure 9E:
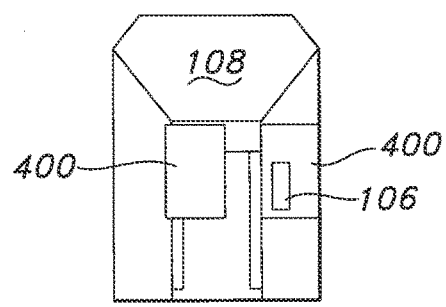

FIG. 9D illustrates that the side tab 400 on the third edge 124 is deployed so that the panel attachment means 106 is used to securely place the third edge against the second end 118 of the barrier panel (i.e., the content covering region). As can be seen in FIG. 9D, the panel attachment means 106 are positioned on the side tabs 400 so they attach to the second end 118 of the barrier panel (i.e., the content covering region) between the spaced apart pull locations 500 of the pull tab system 300. FIG. 9E illustrates that the first edge 120 of the barrier panel 102 is folded over the second end 118. While not necessarily shown to scale, the first edge 120 of the barrier panel 102 upon folding need not extend very far toward the middle of the assembly. Accordingly, it is evident that the third edge 124 and the first edge 120 generally do not overlap. Unlike conventional sterilization wrap in which the edges are intentionally overlapped as generally illustrated in FIGS. 4 and 5, the edges 120 and 124 of the barrier panel are separated by a distance. This difference highlights the importance of the panel attachment means 106 to hold the folded edges 120 and 124 of the barrier panel 102 in place about the content. Moreover, having these edges generally exposed highlights the importance of the fold protection panel 108.

Figure 9F:
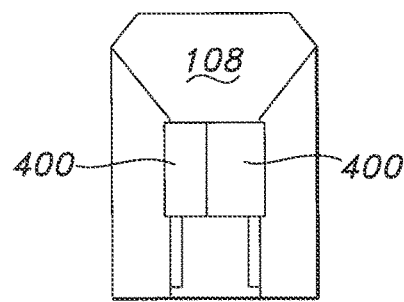
Figure 9G:
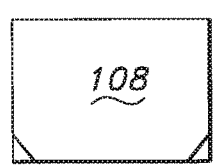

FIG. 9F illustrates that the side tab 400 on the first edge 120 is deployed so that the patent attachment means 106 is used to join this edge to the second end 118 of the barrier panel (i.e., the content covering region). As can be inferred from FIG. 9F, the panel attachment means 106 are positioned on the side tabs 400 so they attach to the second end 118 of the barrier panel (i.e., the content covering region) between the spaced apart pull locations 500 of the pull tab system 300.

Referring again to FIGS. 9D and 9F, the fold protection panel 108 and the portion of the barrier panel 102 between the extremity "E" at the first end 114 of the barrier panel and the pre-determined fold line 116 is folded over bringing the distal end 144 of the fold protection panel 108 over the second end 118 of the barrier panel. In some embodiments, a portion of the material adjacent the first edge 120 and the third edge 124 may be visible. With this configuration, the actual edges 120 and 124 of the barrier panel 102 are fully covered so the edges themselves are less susceptible to being accidently pulled open or breached during normal handling of the package. The fold protection panel is typically secured utilizing conventional tape that is used with sterilization wrap. Desirably, the fold protection panel covers the edges of the barrier protection panel after it is folded around the content to be sterilized to form a package. The fold protection panel covers these edges to prevent a worker inadvertently opening the folded barrier protection panel. In addition, the fold protection panel shields the edges from snags, pulls or other phenomenon that could impart a peel force to these edges that would cause the panel attachment means to detach. That is, the configuration of the multi-panel sterilization assembly utilizes the fold protection panel to protect exposed edges of the barrier panel after the barrier panel has been folded around content to be sterilized to form a package.

Figure 10A:
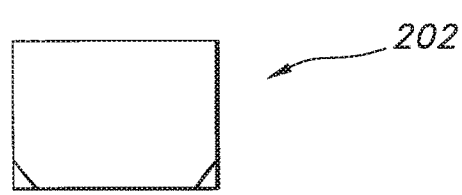
FIGS. 10A to 10D are illustrations of an exemplary sequence of unfolding an exemplary disposable flexible multi-panel sterilization assembly including side tabs and pull tabs having spaced apart pull locations.
Figure 10B:
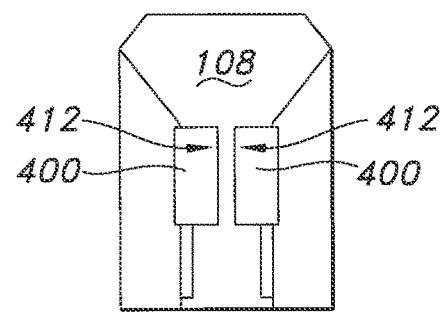
Figure 10C:
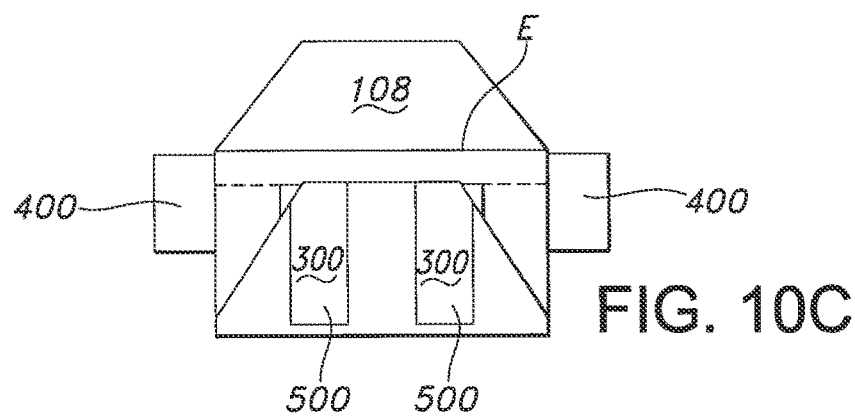
Figure 10D:
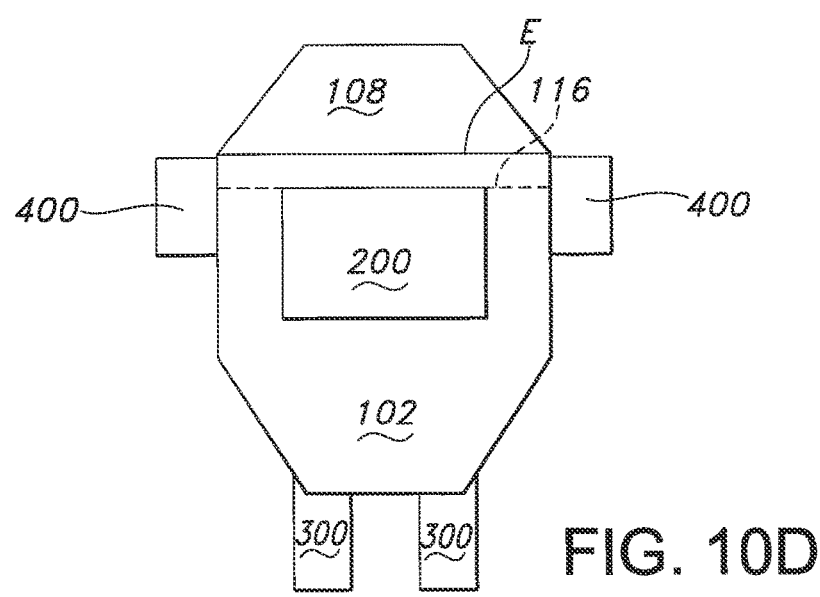

The sequence of unfolding the multi-panel sterilization assembly after it has wrapped around a tray or article and sterilized is generally the reverse of the folding sequence as generally illustrated in FIGS. 10A to 10D. For example, FIG. 10A illustrates a package 202 ready to be unwrapped or unfolded. A conventional tape securing the fold protection panel 108 is broken and the fold protection panel 108 is pulled back to expose the side tabs 400 as illustrated in FIG. 10B. The side tab distal end 412 (or other convenient portion) of each side tab may be grasped and the side tabs 400 may be pulled up and to the side (away from the center) to detach the panel attachment means such that the first edge 120 and the third edge 124 are unfolded to a configuration as generally illustrated by FIG. 10C. This step may be carried out by pulling the side tabs 400 simultaneously or sequentially. Importantly, the location/position of the side tabs 400, the ability to grip the side tabs without compromising sterility, and the leverage and distribution of forces provided by the extended side tabs help the fold protection panel, and the first edge 120 and the third edge 124 of the barrier panel remain in a generally flat, unfolded configuration, which keeps them from folding back up over the content 200.

Referring briefly to FIG. 8C of the drawings, the configuration in which the panel attachment means 106 is located near the proximal tab end 402 provides a grip region "G" between panel attachment means 106 and the distal tab end 412. The distance between the distal tab end 412 and the panel attachment means may range from about ½ inch (e.g., a distance sufficient to avoid meaningful interference between a user's fingers and the panel attachment means) to a distance of up to about 6 inches or more. For example, the distance may be about ¾ inch to about 6 inches. Of course, if the side tab 400 has a non-rectangular shape (e.g., is triangular or semi-circular, etc.), the position of the panel attachment means 106 from the distal end of the side tab will desirably provide a grip region. It is desirable that the panel attachment means 106 is positioned so that it is separated from the proximal tab end 402. For example, the panel attachment means 106 may be positioned so that it is separated from the proximal tab end 402 by a distance ranging from about ¼ inch up to 3 inches or more. During the sequence of unfolding the multi-panel sterilization assembly as illustrated at, for example, in FIGS. 10B and 10C, the separation distance is desirable because it generates disengagement of the panel attachment means from the barrier panel (or other component to which it is attached to keep the sterilization assembly in a folded configuration) prior to unfolding of the edges of the barrier panel.

These distances (i.e., to provide a grip region "G" and the separation between the panel attachment means 106 and the proximal tab end 402) singularly or in combination are also believed to help promote the opening of the multi-panel sterilization assembly (see, for example, FIGS. 10B and 10C) by a motion or orientation that provides primarily peel forces rather than shear forces to separate or disengage the panel attachment means 106. Such a configuration is advantageous because the peel force required to separate the panel attachment means is lower than the shear forces. When mechanical fastening systems such as, for example, hook and loop fasteners are used or when adhesive fastening systems are used in which the adhesive is applied directly to the barrier panel, such a configuration that promotes separation by peel force is thought to reduce the amount of broken fibers which may help reduce the possibility of contamination. The configuration also allows a user to disengage or separate the panel attachment means from the material to which it is attached before the edges of the package (e.g., the first edge 120 and the third edge 124) are unfolded to open the package. Furthermore, the configuration helps prevent a user from inserting a hand into the package under the edges (e.g., the first edge 120 and the third edge 124) to disengage the panel attachment means. The configuration illustrated in FIG. 8C also allows a user some freedom to manipulate the panel attachment means to increase engagement between the mechanical fasteners or adhesive and the material to which it is being attached to during folding—as well as to pull the material taut during folding.

As seen in FIG. 10C, unfolding the side tabs 400 exposes the spaced apart pull locations 500 of the pull tab system 300. Each pull location 500 is grasped at a convenient location or at the position when the pull tab system 300 is secured to the barrier panel with an adhesive tab or sticker and the tab or sticker is pulled up. The pull tab system 300 and the second end 118 of the barrier panel is pulled away from the content 200. Importantly, the spaced apart pull locations 500 help the first edge 120 and the third edge 124 of the barrier panel remain in a generally flat, unfolded configuration which keeps them from folding back up over the content 200.

According to the present invention, the barrier panel may be composed of at least one layer of a breathable nonwoven material. Desirably, the breathable nonwoven material is a laminate composed of a layer of spunbonded filaments, a layer of meltblown fibers, and a layer of spunbonded filaments—also called spunbonded-meltblown-spunbonded material. The method of making these layers is known and described in commonly assigned U.S. Pat. No. 4,041,203 to Brock et al which is incorporated herein in its entirety by reference. The material of Brock et al is a three layer laminate of spunbonded-meltblown-spunbonded layers which is also commonly referred to by the acronym "SMS". The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5-50% of the surface area of the laminate. Desirably, the bonds may occupy about 10-30% of the surface area of the laminate. Other combinations and variations of these materials are contemplated. As a non-limiting example, the inner layer may contain two meltblown layers such that the material may be called "SMMS".

When the barrier panel is composed of or incorporates SMS material(s), the basis weight of the SMS material(s) may be from 1 ounce per square yard or "osy" which is approximately (33 grams per square meter or "gsm") to about 3 osy (100 gsm). For example, the basis weight of the SMS material(s) may be from 1.2 osy (40 gsm) to about 2 osy (67 gsm). As another example, the basis weight of the SMS material(s) may be from 1.4 osy (47 gsm) to about 1.8 osy (60 gsm). The basis weight may be determined in accordance with ASTM D3776-07. Multiple plies or layers of SMS material may be used to provide basis weights ranging from about 2 osy (67 gsm) to about 5 osy (167 gsm).

The permeability of the sheet material of the barrier panel may range from 25 to about 500 cubic feet per minute (CFM) as characterized in terms of Frazier permeability. For example, the permeability of the sheet material barrier panel may range from 50 to about 400 cubic feet per minute. As yet another example, the permeability of the sheet material of the barrier panel may range from 100 to about 300 cubic feet per minute. Alternatively and/or additionally, the permeability of the barrier panel may range from 25 to about 500 cubic feet per minute (CFM) as characterized in terms of Frazier permeability. For example, the permeability of the barrier panel may range from 50 to about 400 cubic feet per minute. As yet another example, the permeability of the barrier panel may range from 100 to about 300 cubic feet per minute. The Frazier permeability, which expresses the permeability of a material in terms of cubic feet per minute of air through a square foot of area of a surface of the material at a pressure drop of 0.5 inch of water (or 125 Pa), was determined utilizing a Frazier Air Permeability Tester available from the Frazier Precision Instrument Company and measured in accordance with Federal Test Method 5450, Standard No. 191A.

When the barrier panel is composed of or incorporates SMS material(s) that have basis weights ranging from about 1 osy (33 gsm) to about 2.6 osy (87 gsm), the permeability of the barrier panel may be lower than 25 cubic feet per minute. For example, when SMS materials having basis weights ranging from about 1 osy (33 gsm) to about 2.6 osy (87 gsm), the permeability of the barrier panel may range from about 20 cubic feet per minute to about 75 cubic feet per minute when determined generally in accordance with ISO 9237:1995 (measured with an automated air permeability machine using a 38 cm² head at a test pressure of 125 Pa,—exemplary air permeability machine is TEXTEST FX 3300 available from TEXTEST AG, Switzerland). If multiple plies or layers of SMS material are used to provide basis weights ranging from about 2 osy (67 gsm) to about 5 osy (167 gsm), the permeability of the barrier panel may range from about 10 cubic feet per minute to about 30 cubic feet per minute when determined generally in accordance with ISO 9237:1995.

As noted above, the flexible multi-panel sterilization assembly 100 may include at least one pull tab system 300 extending from the second end 118 of the barrier panel 102. The pull tab system 300 may be formed of the same material as the barrier panel or may be formed of one or more different materials. The pull tab is a feature that can be grasped by a person to unfold the second end 118 without compromising the sterile field formed by the unfolded content-contacting portions of the barrier panel. The pull tab system 300 may be attached to the barrier panel or it may be integral or unitary with the barrier panel. In an aspect of the invention, the interface or transition of the barrier panel and the attached pull tab system 300 may be bonded or conditioned to result in a stiffening configuration. Such configurations may utilize a seam such as, for example, a stitched seam, an ultrasonic bond seam, adhesive bond seam, thermo-mechanical bond seam (e.g., a bar seal seam), thermal treatments, or combinations thereof to provide sufficient stiffness, rigidity or support to that portion of the barrier panel so that folding or creasing of the barrier panel is reduced or eliminated when force is applied to the pull tab system 300 during unwrapping. This is important to preserve the sterility of the contents during unwrapping. For example, the second edge 122 and the fourth edge 126 illustrated in FIG. 7B may be partially or substantially made to provide such a configuration. As another example, the second edge 122 illustrated in FIG. 8A may be partially or substantially bonded to provide the desired configuration. As yet another example, the second edge 122 and/or the fourth edge 126 and fifth edge 128 illustrated in FIG. 8A may be partially or substantially bonded to provide the desired configuration.

In an embodiment of the invention, the sterilization assembly may further include one or more discrete reinforcement elements in the content receiving region. In addition to reinforcing the barrier panel, the reinforcement element may define an area for receiving content to be sterilized. It is contemplated that the side tabs may extend into the content receiving region to reinforce the barrier panel and/or define an area for receiving content to be sterilized. Accordingly, the following discussion can be applied to the side tab if it is desired for that component to also serve as a reinforcement element in addition to providing a gripping region for the edges of the barrier panel during unfolding of the barrier panel. The reinforcement elements may include one or more layers of materials selected from fibrous webs, impermeable films, permeable or porous films, apertured films, foams and combinations thereof. For example, fibrous webs may include those that are woven and nonwoven. Woven webs may include natural or synthetic materials or blends of the same. As examples, natural materials could be weaves of cotton yarn, and synthetic materials could be weaves of polypropylene, polyester, or nylon yarn and the like. Nonwoven webs may include, for example, spunbond, meltblown, carded webs, wet formed or airlaid webs, or laminates of the same (e.g., spunbond/meltblown/spunbond). Such nonwoven webs may also include natural or synthetic materials or blends of the same. The reinforcement elements include one or more layers of material selected from permeable or impermeable films or laminates of the same. Permeable films may be apertured or be microporous. Apertured films may be obtained through mechanical aperturing, vacuum aperturing, or other commercially available techniques.

Reinforcement elements can be discrete zones of the barrier panel containing additional material or treatments to reduce the likelihood that the barrier panel will be compromised by pressure cuts, pressure holes, tears or the like in the locations where the content is likely to concentrate forces against the material(s) of the barrier panel. It is envisioned that relative to the material(s) of the barrier panel, the reinforcement elements can be less permeable or even impermeable to hot air, steam, or other sterilization gas, while still allowing for proper sterilization and removal of sterilant gas. It has been found that acceptable sterilization and removal of sterilant gas will take place if the permeability of the barrier panel is generally greater than about 25 cubic feet per minute (cfm) as characterized in terms of Frazier permeability. As such, a reinforcement element material that is impermeable or less permeable than the barrier panel is acceptable, as long as the barrier panel is adequately permeable (e.g., greater than about 10 cfm and more desirably greater than about 25 cfm).

The reinforcement elements may also be configured to identify the content receiving region 130 of the barrier panel 102. Alternatively and/or additionally the reinforcement elements may be configured to cooperate with the panel attachment means to identify the content receiving region 130 of the barrier panel 102. For example, the reinforcement elements may be in the form of discrete shapes placed within the content receiving region. FIGS. 11A through 11D are illustrations of exemplary flexible multi-panel sterilization assemblies 100 composed of a barrier panel 102 and a fold protection panel 108 and which further include reinforcement elements 302 (side tabs 400 and pull tab systems 300 not shown).

Figure 11A:
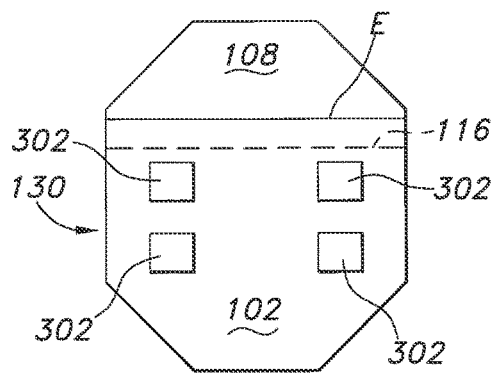
FIGS. 11A to 11D are illustrations of exemplary flexible multi-panel sterilization assemblies showing exemplary reinforcing elements.
Figure 11B:
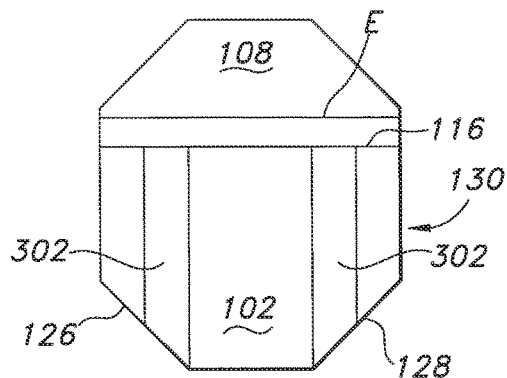
Figure 11C:
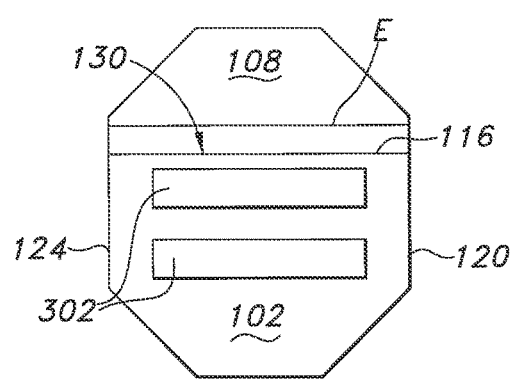

FIG. 11A illustrates a flexible multi-panel sterilization assembly 100 in which four reinforcement elements 302 are positioned at spaced apart locations in the content receiving region 130 of the barrier panel 102 generally at the locations that correspond to the corners of a sterilization tray or similar content. FIG. 11B illustrates a flexible multi-panel sterilization assembly 100 in which two reinforcement elements 302 are positioned at spaced apart locations on the barrier panel 102 extending from the pre-determined fold line 116 to a fourth edge 126 and a fifth edge 128 of the barrier panel 102 generally opposite the pre-determined fold line 116. The two reinforcement elements 302 are positioned in the content receiving region 130 generally at the locations that correspond to the corners of a sterilization tray or similar content. FIG. 11C illustrates a flexible multi-panel sterilization assembly 100 in which two reinforcement elements 302 are positioned at spaced apart locations on the barrier panel 102 generally parallel to the pre-determined fold line 116 between the two panel attachment means 106 at or adjacent a first edge 120 and a third edge 124. The two reinforcement elements 302 are positioned in the content receiving region 130 generally at the locations that correspond to the corners of a sterilization tray or similar content. It is contemplated that the reinforcement elements 302 may extend beyond the edges of the barrier panel and that the extended portion of the reinforcement elements 302 may serve or function as the pull tab system 300. For example, the extended portion may be folded back onto the second opposed side 112 of the barrier panel 102 (see, for example, FIGS. 7C and 8B).

Figure 11D:
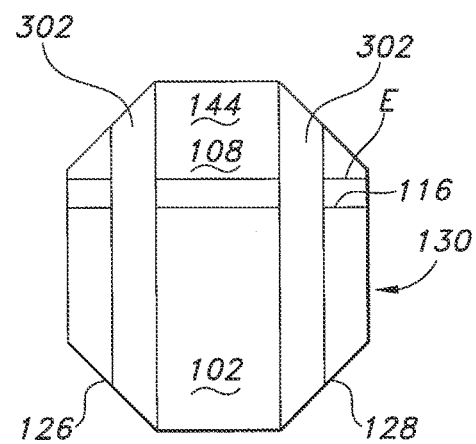

FIG. 11D illustrates a flexible multi-panel sterilization assembly 100 in which two reinforcement elements 302 are positioned at spaced apart locations on the barrier panel 102 and the fold protection panel 108. The two reinforcement elements 302 extend in generally parallel configuration from a distal end 144 of the fold protection panel 108 to a fourth edge 126 and a fifth edge 128 of the barrier panel 102. The two reinforcement elements 302 are positioned in the content receiving region 130 generally at the locations that correspond to the corners of a sterilization tray or similar content.

Figure 12A:
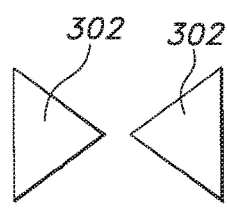
FIGS. 12A to 12B are illustrations of exemplary reinforcing elements.
Figure 12B:
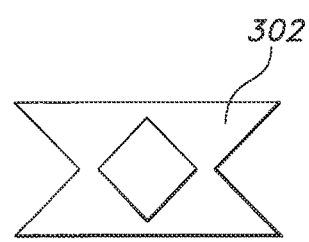

Of course, the reinforcement elements may have a wide variety of shapes, sizes and other configurations. FIGS. 12A and 12B are illustrations of exemplary reinforcement elements 302. FIG. 12A illustrates reinforcement elements 302 having generally triangular configurations. FIG. 12B illustrates an exemplary reinforcement element 302 composed of several overlapping triangular elements. Alternatively and/or additionally, the reinforcement element 302 illustrated in FIG. 12B may be formed by a single piece of material. Other shapes and configurations are contemplated such, for example, "H" patterns, "X" patterns, or the like.

Figure 13:
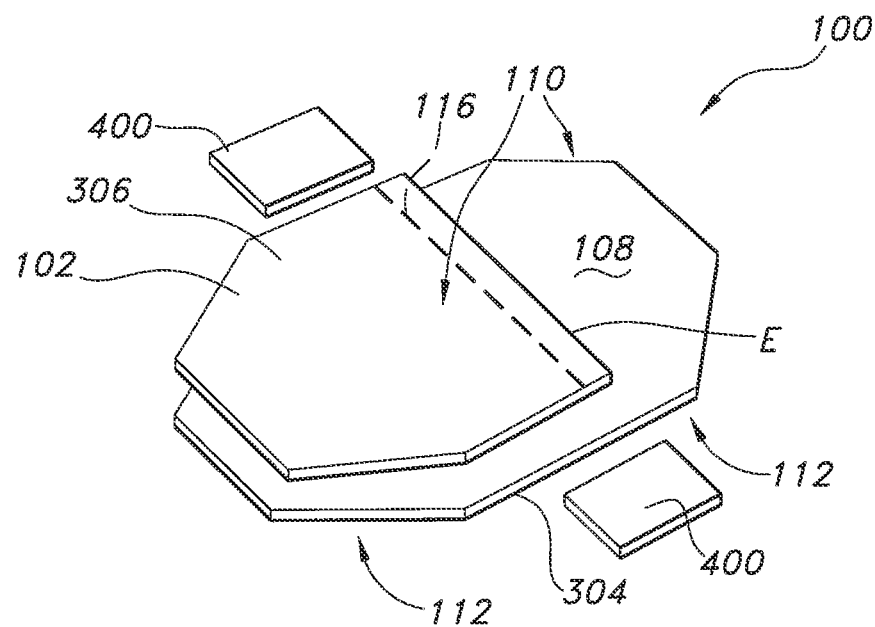
FIG. 13 is an illustration of an exploded or broken apart perspective view of exemplary features of an exemplary flexible multi-panel sterilization assembly.

In an embodiment of the invention, the construction of the disposable flexible multi-panel sterilization assembly may be based on two primary pieces of material. Referring now to FIG. 13, there is shown an illustration of an exemplary disposable flexible multi-panel sterilization assembly 100 in exploded or broken apart view revealing a first piece (layer) 304 of a material and a second piece (layer) 306 of material. In this configuration, the material overlap of the first layer 304 and the second layer 306 define the barrier panel 102. Generally speaking, these layers may be joined by adhesives, ultrasonic bonding, thermo-mechanical bonding or the like. The layers are desirably joined at or adjacent at least two of the edges and along the second end. For example, the layers may be joined along the first edge 120 and the third edge 124. The bonding may be a complete seam or the edge may be partially bonded along only one or a few portions of the edge. Alternatively and/or additionally, the bonding may be intermittent or discontinuous along all or a portion of the respective edge. Of course, other edges may also be bonded or the layers may be bonded together across all or portions of their entire surface area. The region where there is no overlap of the first layer 304 of material and second layer 306 of material forms the fold protection panel 108. Generally speaking, the first layer 304 of material and the second layer 306 of material may be the same material or they may be different materials. For example, the first layer 304 of material may be single layer or multiple layers of spunbond nonwoven material, a lightweight nonwoven laminate material, or a material that lacks the level of barrier properties (or other characteristics) that may be desired for the barrier panel. The second layer 306 of material desirably has a higher level of barrier properties than the first layer 304 of material. For example, the second layer 306 of material may be a laminate of nonwoven fabrics such as "SMS" material. The second layer 306 of material may have a different color and/or pattern than the first layer 304 of material. For example, the first layer 304 of material may have a first color (e.g., a blue color), a dark color, or a specific color on a color scale and the second layer 306 of material may have no color (e.g., white), a second color (e.g., a light color), or a specific color on a color scale that contrasts with the first color. It is contemplated that the color differentiation or contrast between the first layer 304 of material and the second layer 306 of material may be useful to function as an indicator that barrier properties of the barrier panel may be compromised.

Figure 14:
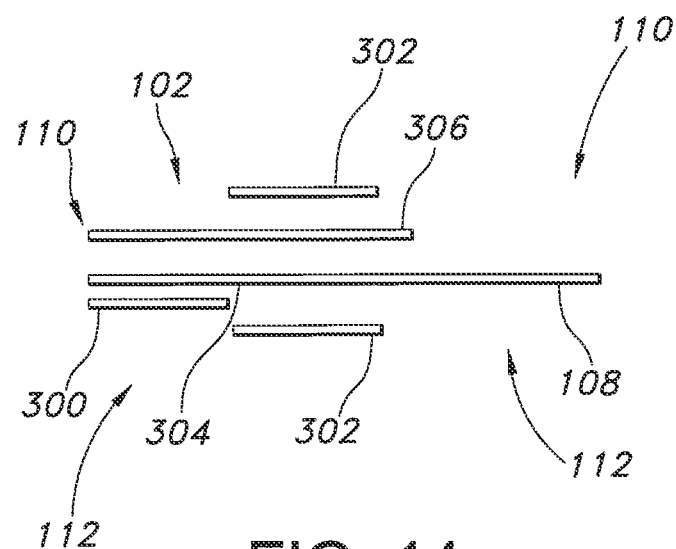
FIG. 14 is an illustration of an exploded or broken apart cross-section view of exemplary features of an exemplary flexible multi-panel sterilization assembly.

Referring now to FIG. 14, there is shown an illustration of an exemplary disposable flexible multi-panel sterilization assembly 100 (side tabs 400 not shown) in exploded or broken apart cross-sectional view revealing a first layer 304 of a material and a second layer 306 of material. In this configuration, the first layer 304 of material and the second layer 306 of material overlap to define the barrier panel 102. The region where there is no overlap of the first layer 304 of material and second layer 306 of material forms the fold protection panel 108. The cross-sectional view illustrates reinforcement elements 302 which may be located directly on the second layer 306 of material. The reinforcement elements 302 may be present on the first surface 110 to desirably identify the content receiving region 130 of the barrier panel 102. Alternatively and/or additionally, the reinforcement elements 302 may be located on the second opposing surface 112 of the barrier panel.

Sterilization wrap has many modes of failure involving tears, cuts, punctures, holes or other breaches. Any failures may have serious consequences. The more common modes of failure are conventionally believed to involve tears, holes or cuts initiating from the sterilization tray or other content that is wrapped by or otherwise enclosed by conventional sterilization wrap fabric. In other words, tears, cuts or holds were believed to begin at the interface between the sterilization tray or other content and the sterilization wrap fabric itself and propagate from the inside of the sterilization wrap fabric penetrating outwardly through the material ultimately creating a breach. Accordingly, much effort has been expended to develop corner guards and other types of protection that is placed between the sterilization tray or other content and the sterilization wrap.

In an aspect of the present invention, it has been discovered that pressure holes and pressure cuts of the type in which the fibers adjacent the hole or cut appear to have been fused or "welded" together most commonly propagate from the outside of a package (i.e., content enclosed by sterilization wrap fabric) rather than propagating the sterilization tray or other content that is wrapped by or otherwise enclosed by conventional sterilization wrap fabric. Desirable embodiments of sterilization assemblies locate the reinforcement elements 302 on the second opposing surface 112 of the barrier panel to provide an additional unexpected advantage because the second opposing surface 112 of the barrier panel 102 is the portion of the disposable flexible multi-panel sterilization assembly 100 that does not contact the content (e.g., sterilization tray) and which typically forms the outside of a wrapped package. Reinforcement elements 302 located on the second opposing surface 112 are thought to provide more efficient protection against pressure holes and pressure cuts because pressure holes and pressure cuts tend to propagate from the outside of a wrapped package. While the inventors should not be held to any particular theory of operation, it is believed that pressure cuts and pressure holes are more frequently caused when content enclosed by sterilization wrap contacts an irregular surface with sufficient force during a single contact event or during multiple contact events such that the irregular surface concentrates the force to generate energy that causes failure.

According to the present invention, the barrier panel, fold protection panel and/or reinforcement elements (if present) may desirably be made of thermoplastic materials that are compatible for recycling. That is, it is desirable that some or all of these components are all made of the same or similar materials such that they can be recycled together. For example, these components may composed of nonwoven materials and/or composite materials (e.g., film and nonwoven laminates) made from of a polyolefin (e.g., polypropylene, polyethylene and combinations thereof). It is also desirable that the side tabs and/or pull tabs (if pull tabs are present) are made of the same or similar materials such that they can be recycled together with the other components (i.e., the barrier panel, fold protection panel and reinforcement elements (if reinforcement elements are present)). However, one or more components (e.g., fold protection panel, reinforcement components, side tabs, panel attachment means, etc.) may be constructed of or include parts made of materials incompatible for recycling together with the other components. According to an aspect of the invention, such incompatible components may be separable from the compatible components so that only the compatible components may be recycled. This may be accomplished by using separable construction adhesives so one or more incompatible components may be stripped off and/or incorporating frangible portions such that the incompatible components may be separated. It is contemplated that the panel attachment means may incorporate incompatible materials. In an embodiment, the panel attachment means may be located in the side tabs. In such a configuration, the side tabs may be joined to the barrier panel utilizing a weak adhesive such that the side tabs may be stripped off with an appropriate level of force (e.g., a level of force that is greater than the side tabs are secured to each other or to a portion of the content covering region in a folded configuration around content for sterilization). Alternatively and/or additionally, the side tabs may include a score line, perforations, or a weakened to thin portion so that the side tab may be easily separated from the barrier panel.

The present invention also encompasses a system or method for releasably securing a flexible multi-panel sterilization assembly about an article for sterilization. The system includes a barrier panel generally as previously described. For example, the barrier panel is composed of a permeable sheet material having barrier properties. The barrier panel includes a first surface and a second opposing surface, a first end and a second end opposite the first end, a first edge and a third edge, each such edge being generally perpendicular to the first end, a second edge that is generally opposite the first end. The barrier panel also includes indicia generally extending from about the first edge to about the third edge—which may be on the barrier panel and/or optional reinforcement elements associated with the barrier panel. The indicia is aligned generally parallel to the extremity "E" of the first end of the barrier panel and located away from this extremity in the direction toward the midpoint of the barrier panel to define an upper boundary of the content receiving region. The barrier panel has a maximum width that is the distance from the first edge to the third edge and a maximum length that is the distance from the first end to the second end, the barrier panel having a midpoint along the length and extending between the first edge and the third edge to generally delineate the barrier panel into a content receiving region extending from approximately the first end to the midpoint and a content covering region extending from the midpoint to approximately the second end.

The system includes a fold protection panel extending from the barrier panel. The fold protection panel includes a proximal end generally adjacent the barrier panel and a distal end generally opposite the proximal end such that the distal end of the fold protection panel covers the one or more panel edges of the barrier panel and the side tabs after folding the side and end portions of the barrier panel.

The system includes side tabs located between the first end and the midpoint of the barrier panel and at or near the first edge and the third edge. The side tabs include grip portions for folding or unfolding the barrier panel. The system also includes barrier panel attachment means. The barrier panel attachment means are desirably located between the upper boundary of the content receiving region and the midpoint of the barrier panel. Even more desirably, the barrier panel attachment means are located on the side tabs away from a proximal end of a side tab to provide a grip portion and away from the distal end of the side tab to facilitate disengagement of the panel attachment means from the barrier panel (or other component to which it is attached to keep the sterilization assembly in a folded configuration) prior to unfolding of the edges of the barrier panel.

According to the system of the present invention, the side tabs and panel attachment means are configured to: (i) join the side tabs to each other and/or to a portion of the content covering region after the barrier panel has been folded at or near its midpoint such that its second end is brought near its first end; (ii) secure the side tabs to each other and/or to a portion of the content covering region in a folded configuration around content for sterilization such that the first edge and third edge are separable by a force of at least about 5 grams-force (gmf) and not greater than 400 gmf; and (iii) disengage the panel attachment means from the side tabs and/or portion of the content covering region to which it is attached prior to unfolding of the edges of the barrier panel.

According to the method of the present invention, the side tabs and panel attachment means are utilized in combination for the steps of: (i) folding the first and third edges via the side tabs up and over the content receiving region after the barrier panel has been folded at or near its midpoint such that its second end is brought near its first end; (ii) securing the side tabs to each other or to a portion of the content covering region via panel attachment means; and (iii) disengaging the panel attachment means from the barrier panel (or other component to which it is attached to keep the sterilization assembly in a folded configurations) by a peel force of at least about 5 grams-force (gmf) and not greater than 400 gmf prior to unfolding of the edges of the barrier panel. Desirably, the configuration of the panel attachment means on the side tabs is such that disengaging the panel attachment means involves gripping a grip region "G" and pulling in a manner that generates primarily peel forces rather than shear forces.

Referring now to FIGS. 16A through 16D of the drawings, there is shown an illustration of a detail of an exemplary side panel and panel attachment means during unfolding of an exemplary sterilization assembly as part of the system or method of the present invention.

FIG. 16 A is a top view illustrating an assembly with the fold protection panel 108 pulled back to expose the side tabs 400 which are joined with the first edge 120 and the third edge 124 (See, for example FIG. 10 B). The panel attachment means 106 are shown in broken lines because they are located beneath the side tabs 400 and are secured to the second end 118 of the barrier panel 102.

Figure 16A:
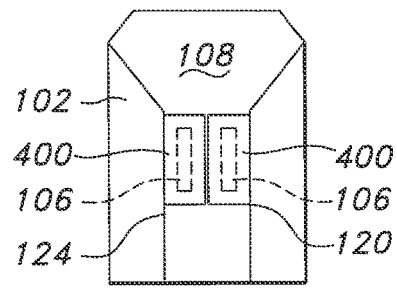
FIG. 16 A is an illustration of a detail of an exemplary side panel and panel attachment means during unfolding of an exemplary sterilization assembly.
FIG. 16C is a side cross-sectional view illustrating detail from FIG. 16B showing features of an exemplary side panel and panel attachment means during unfolding of an exemplary sterilization assembly.
Figure 16B:
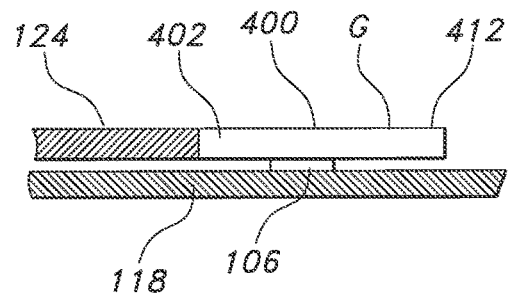

FIG. 16B is a side cross-sectional view illustrating detail from FIG. 16A showing features of an exemplary side panel and panel attachment means. As can be seen in FIG. 16B, the side tab 400 has a distal end 412 with a grip region "G" and a proximal end 402. The proximal end 402 is shown joined to an edge of the barrier panel. In this illustration, which is intended to be a non-limiting example, the proximal end 402 is shown joined to the third edge 124 of the barrier panel.

The side tab 400 incorporates a panel attachment means 106 that secures the side tab (and the edge 124 of the barrier panel) to the second end 118 of the barrier panel 102.

Figure 16C:
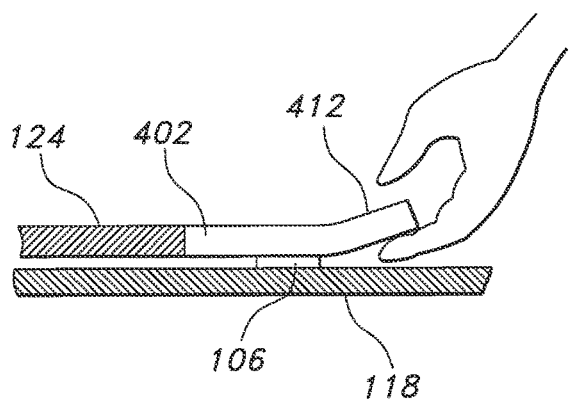
Figure 16D:
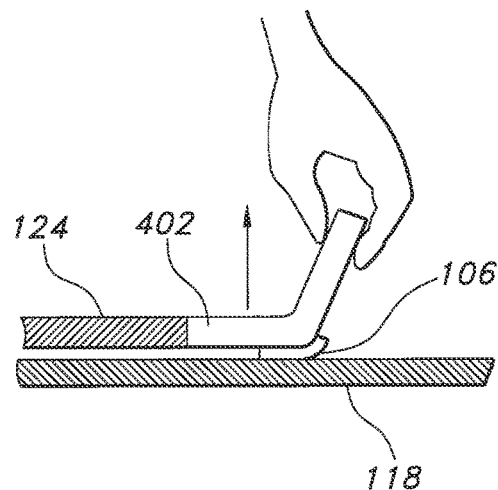

FIG. 16C is a side cross-sectional view illustrating detail from FIG. 16B showing features of an exemplary side panel and panel attachment means during unfolding of an exemplary sterilization assembly by a user. A user grips the grip region G at the distal end 412 of the side tab 400 and begins to pull up the side tab to disengage the panel attachment means 106 from the second end 118 of the barrier panel 102. As illustrated in FIG. 16D, the panel attachment means 106 is positioned so that it is separated from the distal end 412 of the side tab 400 forming a grip region G. This distance between a distal edge of the panel attachment means and the distal tab end may be from about ½ inch to 4 inches or more. The grip region G of the system or method of the present invention is believed to help promote the opening of the multi-panel sterilization assembly by a motion or orientation that provides primarily peel forces rather than shear forces to separate or disengage the panel attachment means 106. Such a configuration is advantageous because the peel force required to separate the panel attachment means is lower than the shear forces.

In addition, the panel attachment means 106 may be positioned so that it is separated from the proximal tab end 402 by a distance ranging from about ¼ inch up to 3 inches or more. During the sequence of unfolding the multi-panel sterilization assembly in the practice of the system or method of the present invention, the separation distance is desirable because it enables disengagement of the panel attachment means from the barrier panel (or other component to which it is attached to keep the sterilization assembly in a folded configurations) prior to unfolding of the edges of the barrier panel.

EXAMPLES

The present invention is further described by the examples which follow. Such examples, however, are not to be construed as limiting in any way either the spirit or the scope of the present invention.

Peel and Shear strength measurements were made for attachment of a commercially available hook fastener, available under the designation Low Profile Hook Fastener 7334 (polyolefin) fastener available from 3M Corporation, St. Paul, Minn., with two different nonwoven laminate fabrics. Each of the nonwoven laminate fabrics are a laminate of two spunbond nonwoven material layers sandwiching a layer of meltblown nonwoven material—also referred to as "SMS" fabrics—available from Kimberly-Clark Corporation, Roswell, Ga.

Samples of the same hook fastener were tested but with three different dimensions—one set had samples 1 inch wide by 4 inches long; a second set had samples ½ inch wide by 4 inches long; and a third set had samples 1 inch wide by 3 inches long. The 3M™ Low Profile Hook Fastener 7334 is believed to have a mushroom-cap type hook element.

The nonwoven laminate fabrics represented the outermost layer or ply of the multi-panel sterilization assembly and had a basis weight of either 1.85 osy (~62 gsm) or 2.57 osy (~86 gsm). Measurements for engagement of the hook fasteners into the 1.85 osy (~62 gsm) and 2.57 osy (~86 gsm) SMS fabrics included fabrics that were steam sterilized and ethylene oxide sterilized.

The measurements for Tables A and B were made in accordance with ASTM D5170-98 (2010) procedures for Peel strength (also called Peel force) and with ASTM D5169-98 (2012) procedures for Shear strength (also called Shear Peak strength, Shear force, or Shear Peak force); these procedures are summarized below. The Peel Strength tests utilized a Crosshead Speed of 12 inches/minute and the Gage Length of 1 inch. The Shear Strength tests utilized a Crosshead Speed of 12 inches/minute and a Gage Length of 3 inches.

Figure 15A:
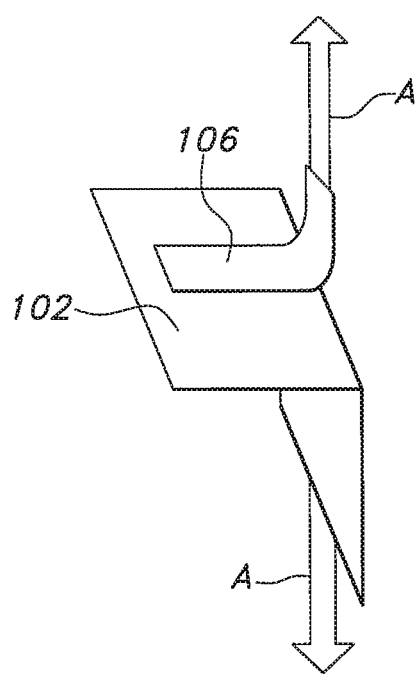
FIG. 15 A is an illustration of an exemplary panel attachment means and a portion of the barrier panel to which it is attached during an exemplary peel test procedure.
Figure 15B:
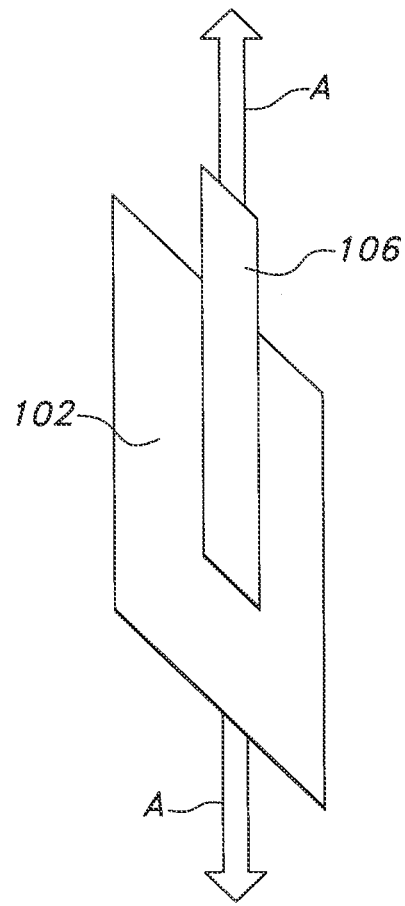

Measurements were made for the hook fastener attached to the 'pattern' (P) and 'anvil' (A) side of the SMS fabrics with the 1 inch dimension of the hook coinciding with the cross-machine direction of the SMS fabrics. For convenience, the machine direction is called the "length direction" of the assembly or the "0 degree orientation", and the cross-machine direction is called the "width direction" of the assembly or the "90 degree" orientation" of the assembly or material. FIG. 15A shows the orientation of the hook fastener against the SMS fabric at the "0 degree" orientation for determining values of peel strength. FIG. 15B shows the orientation of the hook fastener against the SMS fabric at the "0 degree" orientation for determining values of shear strength. That is, in FIGS. 15A and 15B, the hook fastener is pulled in direction of the arrow "A" and the machine direction or "0 degree orientation" of the SMS fabric is also aligned with the arrow "A". The hook fastener was held in the one clamp of the test apparatus (the one that moved) so that its 4 inch length dimension aligned with the direction of the clamp movement and the fabric was held fixed in the other clamp.

Measurements were also made for the 1 inch wide hook fastener attached to the pattern side of the SMS fabrics at two additional different orientations: (i) the 1 inch dimension of the hook coinciding with the CD direction of the fabrics (the length direction of the assembly or "90 degree" orientation); and (ii) the 1 inch dimension at an orientation of "45 degree" with respect to the MD and CD directions of the fabrics. For these non-0 degree orientations, the hook fastener was held in the one clamp of the test apparatus (the one that moved) so that the 4 inch dimension aligned with the direction of the clamp movement and the fabric was held fixed in the other clamp. The hook fastener is pulled in direction of the arrow "A" which is aligned with the respective orientation of the fabric (e.g., "90 degree orientation" or "45 degree orientation").

Peel Test Procedure:

1.1 This test is intended to determine the peel strength required to separate the barrier panel from the panel attachment.

1.2 The test specimen is composed of the panel attachment means 106 and a portion of the barrier panel 102 to which it secures. The test specimen has the panel attachment means directly interfacing with the desired surface of a barrier panel portion. A portion of the barrier panel that at least includes the exterior sheet should have a "length" of at least 5 inches and a "width" of 4 inches with the "length" of the barrier panel being along the direction of desired orientation and the "width" perpendicular to the "length". The external surface of the barrier panel portion, the side that engages the panel attachment means, overlays the panel attachment means to cover it so that the lengths of the barrier panel portion and the panel attachment means coincide and the panel attachment means is approximately centered with respect to the width of the barrier panel portion. Initial mating between the panel attachment means and the barrier panel portion is achieved per the fashion described in ASTM D5170-98 (2010). To engage the panel attachment means and the barrier panel portion together for testing purposes, an appropriate roller traverses over the test specimen through five cycles in the direction of the lengths with the roller centered over the width of the panel attachment means. The appropriate roller device weighs 4.5 pounds and includes a rubber coating around the roller. A suitable roller is part number HR-100 available from Chemsultants International, a business having a location in Mentor, Ohio. After completing the cycles, approximately 1 inch of an end the panel attachment means in the length direction is separated from the barrier panel portion.

1.3 The separated end of the panel attachment means and the adjacent (loose) end of the barrier panel portion are respectively clamped into the two opposing 4-inch wide grips of a tensile testing machine as indicated in FIG. 15A for the peel test. The grips are spaced 1 inch apart. The crosshead speed is 12 inches/min. The panel attachment means is centered and clamped in the moving grip. The force needed to separate the barrier panel portion from the panel attachment means is measured as the grips move away from each other in the directions of the arrows "A". Results are expressed in units of grams-force; higher numbers indicate greater engagement.

Shear Test Procedure 2.1 This test is intended to determine the shear peak forces in grams-force required to separate the barrier panel from the panel attachment means.

2.2 The test specimen is composed of the panel attachment means 106 and the portion of the barrier panel 102 to which it secures. A portion of the barrier panel that at least includes the exterior sheet should have a "length" of at least 5 inches with the "length" of the barrier panel being along the direction of desired orientation and a "width" that is 4 inches and perpendicular to the "length". The external surface of the barrier panel portion, the side that engages the panel attachment means, overlays the panel attachment means to cover 2 inches of it in the length direction with the length directions coinciding; the panel attachment means is approximately centered with respect to the width of the barrier panel portion. Initial mating between the panel attachment means and the barrier panel portion is achieved per the fashion described in ASTM D5169-98 (2012). To engage the panel attachment means and the barrier panel portion together for testing purposes, an appropriate roller traverses over the test specimen through five cycles (note that—three cycles are specified in ASTM D5169-98 (2012)) in the direction of the lengths with the roller centered over the width of the panel attachment means.

2.3 The unattached end of the panel attachment means is centered and clamped into the 4-inch moving grip of a tensile testing machine and the opposing end of the barrier panel portion is clamped into the other 4-inch grip of a tensile testing machine as illustrated in FIG. 15B. The grips are spaced 3 inches apart. The crosshead speed is 12 inch/minute. The force to separate the barrier panel portion from the panel attachment means is measured as the grips move away from each other in the directions of the arrows "A". Results are expressed in units of grams-force; higher numbers indicate greater engagement.

The results for peel and peak shear forces are listed in Tables A and B.

TABLE A

Peel force, grams-force

| | Pattern Side | | | | | | | Anvil | |
|---|---|---|---|---|---|---|---|---|---|
| | Hook width | | | | | | | | |
| | 1" | 1" | 1" | 1" | 1" | 1" | ½" | 1" | 1" |
| | SMS fabric, osy | | | | | | | | |
| | 1.85 | 1.85 | 1.85 | 2.57 | 2.57 | 2.57 | 1.85—sterilized (S) | 1.85 | 2.57 |
| Test | Orientation, degree | | | | | | | | |
| Rep: | 0 | 45 | 90 | 0 | 45 | 90 | 0 | 0 | 0 |
| 1 | 20.59 | 25.79 | 28.72 | 61.37 | 19.37 | 47.83 | 11.86 | 3.79 | 1.2 |
| 2 | 4.91 | 22.45 | 58.63 | 24.99 | 16.37 | 38.91 | 12.82 | 4.48 | 2.03 |
| 3 | 11.88 | 23.26 | 53.77 | 19.89 | 19.39 | 37.07 | 9.85 | 2.92 | 3.05 |
| 4 | 15.65 | 15.4 | 63.55 | 28.1 | 9.03 | 49.96 | 7.5 | 2.05 | 2.77 |
| 5 | 12.39 | 13.99 | 52.65 | 20.97 | 15.84 | 34.04 | 11.42 | 2.51 | 1.99 |
| 6 | 15.1 | 22.55 | 61.36 | 23.73 | 9.13 | 36.36 | 8.34 | 3.79 | 2.43 |
| 7 | 10.65 | 23.01 | 45.67 | 19.08 | 6.32 | 40.83 | 6.82 | 2.9 | 4.33 |
| 8 | 10.25 | 11.89 | 46.25 | 19.62 | 17.36 | 43.45 | 9.57 | 2.92 | 1.69 |
| 9 | 11.12 | 11.91 | 83.01 | 23.3 | 9.38 | 38.12 | 8.65 | 3.73 | 1.96 |
| 10 | 13.07 | 15.35 | 48.31 | 17.39 | 32.54 | 42.86 | 16.97 | 2.3 | 2.12 |
| Avg | 12.56 | 18.56 | 54.19 | 25.84 | 15.47 | 40.94 | 10.38 | 3.149 | 2.36 |
| Std | 4.09 | 5.32 | 14.20 | 12.88 | 7.67 | 5.10 | 3.01 | 0.78 | 0.87 |

TABLE B

Shear Peak force, grams-force

| | Pattern | | | | | | | Anvil | |
|---|---|---|---|---|---|---|---|---|---|
| | Hook width | | | | | | | | |
| | 1" | 1" | 1" | 1" | 1" | 1" | ½" | 1" | 1" |
| | SMS fabric, osy | | | | | | | | |
| | 1.85 | 1.85 | 1.85 | 2.57 | 2.57 | 2.57 | 1.85—S | 1.85 | 2.57 |
| | Orientation, degree | | | | | | | | |
| | 0 | 45 | 90 | 0 | 45 | 90 | 0 | 0 | 0 |
| 1 | 3737.4 | 2218.9 | 3963.1 | 2610.8 | 3277.5 | 2866.5 | 3907.2 | 297.6 | 54.5 |
| 2 | 2714.5 | 4170.1 | 3591.5 | 2913.8 | 5146.9 | 3102.5 | 3652.0 | 1251.1 | 118.7 |
| 3 | 1748.2 | 3710.4 | 5288.0 | 1332.3 | 3924.3 | 2491.5 | 3954.7 | 439.8 | 87.4 |
| 4 | 2350.9 | 3134.2 | 4350.7 | 3293.6 | 4954.6 | 2659.7 | 3908.7 | 3734.9 | 43.1 |
| 5 | 2800.2 | 2369.8 | 2692.5 | 2215.5 | 5155.4 | 4401.9 | 2852.9 | 1277.9 | 34.0 |
| 6 | 3184.3 | 2224.8 | 3437.3 | 3306.1 | 3825.8 | 2157.4 | 2784.6 | 3389.7 | 122.4 |
| 7 | 4238.8 | 2938.1 | 6630.2 | 4193.1 | 5604.9 | 3483.8 | 4586.7 | 141.0 | 32.3 |
| 8 | 3678.9 | 3346.2 | 4351.0 | 2045.7 | 3112.6 | 4306.4 | 3890.5 | 253.2 | 4.9 |
| 9 | 4344.2 | 3199.6 | 5215.5 | 4103.5 | 5276.8 | 3062.7 | 3562.9 | 1128.8 | 3.6 |
| 10 | 2038.0 | 2881.2 | 5639.5 | 3205.0 | 4800.4 | 3253.0 | 3544.2 | 870.2 | 5.4 |
| Avg | 3083.5 | 3019.3 | 4515.9 | 2921.9 | 4507.9 | 3178.5 | 3664.4 | 1278.4 | 50.6 |
| Std | 903.4 | 638.9 | 1179.5 | 898.7 | 892.8 | 727.9 | 533.6 | 1277.6 | 44.9 |

The results reported in Tables A and B show that the hook fastener engages the pattern side of the fabric more than the anvil side. (The anvil side of the fabric is that surface that contacts a smooth calender roll during thermal point bonding; the pattern side of the fabric is the surface of the fabric that contacts the three dimensional patterned roll, and hence the pattern side takes on an imprint of the patterned roll.) Since this sidedness determines the peel and shear values, the surface of the fabric that forms the external surface of the exterior sheet in the assembly is an important design factor when using hook fasteners as the panel attachment means. In addition to fabric factors, the hook element and its spacing (in an array or arrays) are important for delivering sufficient attachment and detachment criteria.

While other types of hook fasteners where evaluated with the range of suitable SMS fabrics, the certain 3M hook fastener gave acceptable attachment and detachment in simulated use evaluations for the pattern surfaces of the 1.85 and 2.57 osy SMS fabrics. For Peel force, the minimum force is 4.91 grams (Table R). For Shear Peak force, the minimum force is 1332 grams. Because orientation of the fabric with respect to the hook fastener shows differences, as is most evident by the 0 and 90 degree Peel forces for both tested fabrics, this can be another influencing factor to consider in selection of fabric and fastener combination and their positioning for use in acceptable assemblies.

The values for the 1 inch versus ½ inch wide hook fastener engagement into the same type of fabric (the 1.85 osy SMS) are concluded to be overlapping. One procedural step in preparing the samples for testing is believed to be an influencing factor: per the ASTM procedures, the same preparatory weighted device rolls over the hook fastener to press it into the fabric for both the ½ and 1 inch strips, therefore the ½ inch wide strip sees more compressive pressure than the 1 inch wide strip. This greater pressure for the ½ inch wide fastener likely imparts more penetration and hence more individual hook element engagement with the fabric than the 1 inch strip, as most evident by the Shear Peak values. Again, this emphasizes the importance of achieving sufficient engagement between the fastener and the fabric as opposed to focusing strictly on dimensions and parameters of the hook fastener and fabrics.

Additional peel measurements involved the Hook Fastener 7334 with dimensions of 1 inch wide by 4 inches long and 1 inch wide by 3 inches long against 1.85 osy and 2.57 osy SMS fabrics. The SMS fabrics included those with exposure to sterilization treatments via steam and ethylene oxide. The peel force measurements were conducted in a similar specimen preparation manner and with the crosshead speed described for the PEEL TEST PROCEDURE but with these modifications: the hook fasteners were supported by side tabs via adhesive bonding between the non-hook side of the fasteners and the surface of the side tabs (the side tabs were 1.85 osy when the barrier panel fabric was 1.85 osy, and 2.57 osy SMS fabric when the barrier panel fabric was 2.57 osy); the separation of the hooks from the SMS fabric was across the 1-inch dimension of the hook fastener, that is the 1-inch dimension of the hook fastener was aligned with the arrow "A" of FIG. 15; the engaged SMS (pattern side)

and supporting side tab were trimmed to 4 inches in the 4- or 3-inch dimension of the hook fastener after specimen preparation; and, unengaged ends of the specimen were clamped in the 4-inch grips with the engaged hook fastener and SMS fabric centered between the grips.

Table C gives the results where the gmf values are averages of 30 individual tests and "Std Dev" is the standard deviations of those 30 tests. The Sterilization treatments denoted as "none" represent as-made fabric, "H2O 1-3" represent respective conventional steam sterilization cycles used by hospitals, i.e. H2O 1=pre-vacuum steam at 273° F. for 3 min, H2O 2=pre-vacuum steam for 270° F. for 4 min, H2O 3=pre-vacuum steam 273° F. for 30 min, and "EO" represents exposure to ethylene oxide sterilization conditions. Observations of opening (unwrapping) wrapped sterilization assemblies, that had the Table U fabrics as the exterior surfaces and the Table U panel fastening means, showed acceptable aseptic opening and no difficulties in disengaging the hook fasteners from the panel barriers. Such observations point to all peel force values for Table U, i.e. average values and upper and lower limits (average plus or minus the corresponding Std Dev) as acceptable values for end-users to disengage panel attachment means from barrier panels without difficulty.

TABLE C

Peel Force, grams-force

| | | 4" × 1" hook | | 3" × 1" hook | |
|---|---|---|---|---|---|
| Fabric, osy | Sterilization treatment | gmf | +/−Std Dev | gmf | +/−Std Dev |
| 1.85 | none | 134 | 42 | 41 | 20 |
| 1.85 | H2O 1 | 152.8 | 49 | 110 | 32 |
| 1.85 | H2O 2 | 106 | 35 | 119 | 46 |
| 1.85 | H2O 3 | 127 | 33 | 98 | 19 |
| 1.85 | EO | 175 | 33 | 127 | 48 |
| 2.57 | none | 182 | 49 | 147 | 41 |
| 2.57 | H2O 1 | 108 | 31 | 160 | 37 |
| 2.57 | H2O 2 | 119 | 32 | 160 | 33 |
| 2.57 | H2O 3 | 110 | 32 | 156 | 28 |
| 2.57 | EO | 238 | 67 | 296 | 51 |

Additional shear force measurements were made involving the 4 and 3 inch long by 1 inch wide hook fasteners and the 1.85 osy and 2.57 osy SMS fabrics of Table C. The SMS fabrics were exposed to the same sterilization treatments as described for Table C.

The shear force measurements were conducted in a similar specimen preparation manner and with the crosshead speed described for the SHEAR TEST PROCEDURE but with these modifications: the hook fasteners were supported on side tabs via adhesive bonding between the non-hook side of the fasteners and the surface of the side tabs as described for Table C values; the external surface of the barrier panel portion fabric (SMS) overlaid the entire side tab supported hook fastener and the machine-direction of the barrier panel fabric was aligned to the length dimension of the hook fastener; and, the engaged SMS fabric and supported hook fastener test specimen was then positioned with the 1 inch width of the hook fastener centered between the grips and the SMS barrier fabric clamped in the non-moving grip and the side tab supporting the hook fastener clamped in the moving grip.

The resulting average values for 30 individual tests and corresponding standard deviations (Std Dev) are given in Table D. The opening observations previously described similarly point to all these shear force values (lower and upper limits included) as acceptable values for end-users to disengage panel attachment means from barrier panels of the invention without difficulty.

TABLE D

Shear force, grams-force

| | | 4" × 1" hook | | 3" × 1" hook | |
|---|---|---|---|---|---|
| Fabric, osy | Sterilization treatment | gmf | +/−Std Dev | gmf | +/−Std Dev |
| 1.85 | none | 4436 | 802 | 2386 | 1104 |
| 1.85 | H2O 1 | 6418 | 812 | 6538 | 1059 |
| 1.85 | H2O 2 | 6750 | 1534 | 6653 | 1292 |
| 1.85 | H2O 3 | 5820 | 1327 | 6472 | 1662 |
| 1.85 | EO | 6919 | 1366 | 5756 | 1110 |
| 2.57 | none | 6995 | 1609 | 6654 | 1484 |
| 2.57 | H2O 1 | 8884 | 2374 | 8496 | 1737 |
| 2.57 | H2O 2 | 9651 | 2011 | 8785 | 1166 |
| 2.57 | H2O 3 | 7122 | 1319 | 9243 | 1575 |
| 2.57 | EO | 11665 | 1776 | 10010 | 1496 |

As previously mentioned, the peel force between the barrier panel and the panel attachment means needs to be less than the peel strength of the bond that joins the panel attachment means to its support. Table E illustrates acceptable peel strengths in terms of gram-force (gmf) for the bond between hook fasteners (on the surface opposing that involved in engagement with the barrier panel) and supporting side tabs. These bond values, expressed as peel forces, were measured in a manner similar to that described for the PEEL TEST PROCEDURE with the length of the hook fastener and the MD direction of the fabric in the side tab coinciding and these exceptions: each test specimen consisted of the hook fastener 7334 and a supporting side tab of 1.85 or 2.57 osy SMS fabric; the peel force measured the separation of the adhesive bond between the non-hook side of the fastener from the SMS fabric; and, the hook fastener was manually separated from the supporting side tab and the hook fastener was clamped with its 4-inch dimension in the moving grip and the side tab clamped in the non-moving grip.

In Table E, the "Fabric" denotes the SMS fabric of the supporting side tab (as opposed to the barrier panel as in table C and D). The hook fasteners bonded to the side stabs were exposed to the same sterilization treatments as described for Table C. As seen by comparing the respective barrier panel and side tab combinations (i.e. 1.85 osy fabrics to each other, 2.57 osy fabric to each other), the Table C values are less than the Table E values. The Table E peel forces were also sufficient to secure (bond) the hook fasteners to the side tabs to ensure no separation during the shear force evaluations that gave Table W results.

TABLE E

Peel force separating supported hook fastener from support, grams-force

| | | 4" × 1" hook | | 3" × 1" hook | |
|---|---|---|---|---|---|
| Fabric, osy | Sterilization treatment | gmf | +/−Std Dev | gmf | +/−Std Dev |
| 1.85 | none | 617 | 73 | 443 | 41 |
| 1.85 | H2O 1 | 488 | 46 | 395 | 40 |
| 1.85 | H2O 2 | 473 | 53 | 390 | 51 |
| 1.85 | H2O 3 | 522 | 70 | 421 | 38 |
| 1.85 | EO | 537 | 46 | 453 | 55 |
| 2.57 | none | 696 | 237 | 647 | 332 |

TABLE E-continued

Peel force separating supported hook fastener from support, grams-force

| Fabric, osy | Sterilization treatment | 4" × 1" hook gmf | +/−Std Dev | 3" × 1" hook gmf | +/−Std Dev |
|---|---|---|---|---|---|
| 2.57 | H2O 1 | 567 | 86 | 727 | 87 |
| 2.57 | H2O 2 | 506 | 79 | 732 | 81 |
| 2.57 | H2O 3 | 531 | 89 | 762 | 97 |
| 2.57 | EO | 581 | 153 | 724 | 165 |

Thus, exemplary embodiments of the invention are presented herein; however, the invention may be embodied in a variety of alternative forms, as will be apparent to those skilled in the art. To facilitate understanding of the invention, and provide a basis for the claims, various figures are included in the description. The figures are not drawn to scale and related elements may be omitted so as to emphasize the novel features of the invention. Structural and functional details depicted in the figures are provided for the purpose of teaching the practice of the invention to those skilled in the art and are not intended to be considered limitations.

While particular embodiments of the present invention have been described herein; it will be apparent to those skilled in the art that alterations and modifications may be made to the described embodiments without departing from the scope of the appended claims.

What is claimed is:

1. A flexible multi-panel sterilization assembly comprising:
   a barrier panel comprising a nonwoven permeable sheet material having barrier properties and susceptible to heat set during sterilization, the barrier panel including:
   a first surface and a second opposing surface,
   a first end and a second end opposite the first end,
   a first edge and a third edge, each such edge being generally perpendicular to the first end, and
   a second edge that is generally opposite the first end,
   the barrier panel having a maximum width that is the distance from the first edge to the third edge and a maximum length that is the distance from the first end to the second end, the barrier panel having a midpoint along the length and extending between the first edge and the third edge to generally delineate the barrier panel into a content receiving region extending from approximately the first end to the midpoint and a content covering region extending from the midpoint to approximately the second end;
   side tabs located between the first end and the midpoint of the barrier panel and at or near the first edge and the third edge; the side tabs including grip portions for folding or unfolding the barrier panel;
   a pull tab system including a first pull tab spaced apart from at least a second pull tab, wherein the pull tab system is located at the second end of the barrier panel, wherein the first pull tab is positioned adjacent the first edge of the barrier panel and the second pull tab is positioned adjacent the third edge of the barrier panel, further wherein the first pull tab and the second pull tab are configured to extend beyond the second end of the barrier panel when loose ends of the first pull tab and the second pull tab are grasped during unwrapping of a wrapped sterilization assembly; and
   a fold protection panel in juxtaposed communication with the barrier panel, the fold protection panel comprising a permeable sheet material, the fold protection panel including:
   a proximal end generally adjacent the first end of the barrier panel,
   a distal end generally opposite the proximal end; and
   at least a first edge and a second edge extending away from the proximal end, the fold protection panel having a maximum width that is the greatest distance from the first edge to the second edge and a maximum length that is the distance from the proximal end to the distal end, such that:
   after the barrier panel has been folded at or near the barrier panel's midpoint so the barrier panel's second end is brought towards its first end and the side tab on the first edge and the side tab on the third edge are folded over the barrier panel towards or overlapping each other to form at least a partial enclosure, the distal end of the fold protection panel is configured to cover at least the first edge and the third edge of the folded barrier panel.

2. The sterilization assembly of claim 1, wherein the barrier panel has a fourth edge.

3. The sterilization assembly of claim 2, wherein the barrier panel includes a fifth edge.

4. The sterilization assembly of claim 1, further comprising barrier panel attachment means to secure portions of the first edge and the third edge to each other or to a portion of the content covering region after the barrier panel has been folded at or near its midpoint such that its second end is brought towards its first end.

5. The sterilization assembly of claim 1, wherein the side tabs are located on the second surface of the barrier panel.

6. The sterilization assembly of claim 4, wherein:
   the barrier panel further comprises indicia aligned generally parallel to the first end of the barrier panel and located away from the first end in the direction toward the midpoint of the barrier panel to define an upper boundary of the content receiving region; and
   each side tab further comprises a proximal tab end generally at or adjacent the respective first edge and third edge of the barrier panel, each side tab defining a tab width at the proximal tab end.

7. The sterilization assembly of claim 4, wherein the panel attachment means are selected from adhesive tape, double-sided adhesive tape, cohesive materials, hook and loop fastening systems, mechanical fastening systems, snaps, clips, magnets, catches, slots and tabs, and combinations thereof.

8. The sterilization assembly of claim 4, wherein the panel attachment means attach to the content covering region between the spaced apart pull tabs.

9. The sterilization assembly of claim 1, wherein the fold protection panel has at least a third edge located at or along its distal end.

10. The sterilization assembly of claim 6, further comprising barrier panel attachment means to join the side tabs to each other or to a portion of the content covering region, at least one barrier panel attachment means being located on a portion of the side tab so the barrier panel attachment means is configured for positioning over the content covering region between the midpoint of the barrier panel and the upper boundary of the content receiving region.

11. The sterilization assembly of claim 10, wherein the barrier panel attachment means are configured to secure the side tabs to each other or to a portion of the content covering region such that it requires a peel force of between about 5 to about 400 grams-force to unsecure the side tabs from each other or from a portion of the content covering region.

12. The sterilization assembly of claim 11, wherein the barrier panel attachment means are configured to secure the side tabs to each other or to a portion of the content covering region such that it requires a shear force of at least about 1332 grams-force to unsecure the side tabs barrier from each other or from a portion of the content covering region.

13. A system for wrapping an article for sterilization, the system comprising:
- a barrier panel comprising a nonwoven permeable sheet material having barrier properties and susceptible to heat set during sterilization, the barrier panel including:
  - a first surface and a second opposing surface,
  - a first end and a second end opposite the first end,
  - a first edge and a third edge, each such edge being generally perpendicular to the first end,
  - a second edge that is generally opposite the first end, and
  - indicia generally extending from about the first edge to about the third edge of the barrier panel, the indicia aligned generally parallel to the first end of the barrier panel and located away from the first end in the direction toward the midpoint of the barrier panel to define an upper boundary of the content receiving region,
  - the barrier panel having a maximum width that is the distance from the first edge to the third edge and a maximum length that is the distance from the first end to the second end, the barrier panel having a midpoint along the length and extending between the first edge and the third edge to generally delineate the barrier panel into a content receiving region extending from approximately the first end to the midpoint and a content covering region extending from the midpoint to approximately the second end;
- side tabs located between the first end and the midpoint of the barrier panel and at or near the first edge and the third edge; the side tabs including grip portions for folding or unfolding the barrier panel;
- a fold protection panel extending from the barrier panel, the fold protection panel including:
  - a proximal end generally adjacent the barrier panel,
  - a distal end generally opposite the proximal end; wherein the distal end of the fold protection panel covers the one or more panel edges of the barrier panel and the side tabs after folding the side and end portions of the barrier panel;
- barrier panel attachment means on the side tabs, the barrier panel attachment means at a location between the upper boundary of the content receiving region and the midpoint of the barrier panel; and
- a pull tab system including a first pull tab spaced apart from at least a second pull tab, wherein the pull tab system is located at the second end of the barrier panel, wherein the first pull tab is positioned adjacent the first edge of the barrier panel and the second pull tab is positioned adjacent the third edge of the barrier panel, further wherein the first pull tab and the second pull tab are configured to extend beyond the second end of the barrier panel when loose ends of the first pull tab and the second pull tab are grasped during unwrapping of a wrapped sterilization assembly;
- the side tabs and panel attachment means configured to:
  - join the side tabs to each other and/or to a portion of the content covering region after the barrier panel has been folded at or near its midpoint such that its second end is brought near its first end;
  - secure the side tabs to each other and/or to a portion of the content covering region in a folded configuration around content for sterilization such that the first edge and third edge are separable by a force of at least about 5 grams-force (gmf) and not greater than 400 gmf; and
  - disengage the panel attachment means from the side tabs and/or portion of the content covering region to which it is attached prior to unfolding of the edges of the barrier panel.

* * * * *